(12) United States Patent
Tripathi et al.

(10) Patent No.: US 12,268,676 B2
(45) Date of Patent: Apr. 8, 2025

(54) ANTIVIRAL APPLICATIONS OF PICOLINIC ACID AND ITS DERIVATIVES

(71) Applicant: INDIAN INSTITUTE OF SCIENCE, Karnataka (IN)

(72) Inventors: Shashank Tripathi, Bengaluru (IN); Rohan Narayan, Bengaluru (IN); Abhijith Biji, Bengaluru (IN); R. S. Rajmani, Bangalore (IN)

(73) Assignee: Indian Institute of Science, Karnataka (IN)

( * ) Notice: Subject to any disclaimer, the term of this patent is extended or adjusted under 35 U.S.C. 154(b) by 463 days.

(21) Appl. No.: 17/578,968

(22) Filed: Jan. 19, 2022

(65) Prior Publication Data

US 2022/0226292 A1    Jul. 21, 2022

Related U.S. Application Data

(60) Provisional application No. 63/139,696, filed on Jan. 20, 2021.

(51) Int. Cl.
*A61K 31/4402* (2006.01)
*A61P 31/16* (2006.01)

(52) U.S. Cl.
CPC .......... *A61K 31/4402* (2013.01); *A61P 31/16* (2018.01)

(58) Field of Classification Search
None
See application file for complete search history.

(56) References Cited

U.S. PATENT DOCUMENTS

2009/0241222 A1  9/2009  Fernandez-Pol et al.
2010/0015174 A1  1/2010  Fernandez-Pol et al.

FOREIGN PATENT DOCUMENTS

WO  2002020486  5/2002
WO  1997024121  1/2010

OTHER PUBLICATIONS

Hanson et al., bioRxiv, pp. 1-23, Digital Object ID: 10.1101/2020.06.16.154708, URL: https://www.biorxiv.org/, (Year: 2020).*
Subudhi et al., Viruses, vol. 10, No. 235, pp. 1-40 (Year: 2018).*
Wolf et al., PNAS, vol. 107, No. 7, pp. 3157-3162, Feb. 16, 2010, www.pnas.org/cgi/doi/10.1073/pnas.0909587107 (Year: 2010).*

PCT/IB2022/050463 International Search Report, mail date May 23, 2022, 5 pages.
PCT/IB2022/050463 Written Opinion of the International Seaching Authority, mail date May 23, 2022, 7 pages.
Aggett et al. (1989) "An in Vitro Study of the Effect of Picolinic Acid on Metal Translocation across Lipid Bilayers 1-3," American Institute of Nutrition, pp. 1432-1437.
Blasi et al. (1993) "Protective Effect of Picolinic Acid on Mice Intracerebrally Infected with Lethal Doses of Candida albicans," Antimicrobial Agents and Chemotherapy, vol. 37, No. 1, pp. 2422-2426.
Bosco et al. (2003) "Macrophage Activating Properties of the Tryptophan Catabolite Picolinic Acid," Advances in Experimental Medicine and Biology, vol. 52, pp. 55-65.
Fernandez-Pol (1978) "Morphological Changes induced by Picolinic Acid in Cultured Mammalian Cells," Experimental and Molecular Pathology, vol. 29, pp. 348-357.
Fernandez-Pol and Hamilton (2001) "Antiviral, cytotoxic and apoptotic activities of picolinic acid on human immunodeficiency virus-1 and human herpes simplex virus-2 infected cells," Anticancer Res., vol. 21, No. 6A, pp. 3779-3776 Abstract Only.
Fernandez-Pol and Johnson (1977) "Selective Toxicity Induced by Picolinic Acid in Simian Virus 40-transformed Cells in Tissue Culture," Cancer Research, vol. 37, pp. 4276-4279.
Kreiger (1980) "Picolinic acid in the treatment of disorders requiring zinc supplementation," Nutrition Reviews, vol. 38, No. 4, pp. 148-150.
Melillo et al. (1996) "Immunobiology of Picolinic Acid," Advances in Experimental Medicine and Biology, vol. 398, pp. 135-141.
Sharma et al. (2016) "Inhibition of chikungunya virus by picolinate that targets viral capsid protein," Virology, vol. 498, pp. 265-276.
Shibata and Fukuwatari (2014) "Large Amounts of Picolinic Acid Are Lethal but Small Amounts Increase the Conversion of Tryptophan-Nicotinamide in Rats," J. Nutr Sci, Vitaminol, vol. 60, pp. 334-339.
Testa et al. (1985) "The iron-chelating agent picolinic acid enhances transferrin receptors expression in human erythroleukaemic cell lines," British Journal of Haematology, vol. 60, pp. 491-502.

* cited by examiner

*Primary Examiner* — Zinna Northington Davis
(74) *Attorney, Agent, or Firm* — Mandar A. Joshi; Bozicevic, Field & Francis LLP

(57) ABSTRACT

The present disclosure provides methods for inhibiting entry of a virus into a host cell using picolinic acid or a salt or derivative thereof. The present disclosure also provides methods for treating or preventing a viral infection in a subject by administering picolinic acid or a salt or derivative thereof. In particular, the methods of the present disclosure are effective for enveloped viruses and syncytium-forming viruses. In some embodiments, the present disclosure provides methods of treating or preventing a SARS CoV-2, Influenza A virus, human parainfluenza virus, herpes simplex virus, Japanese encephalitis virus, Zika virus, or a flavivirus infection.

16 Claims, 31 Drawing Sheets

ANTIVIRAL APPLICATIONS OF PICOLINIC ACID AND ITS DERIVATIVES

FIELD OF THE DISCLOSURE

The present disclosure relates to methods and compositions for treating or preventing viral infections. In particular, the present disclosure relates to use of picolinic acid or a salt or derivative thereof or compositions comprising said compounds for treating or preventing viral infections caused by enveloped viruses such as SARS-CoV-2 virus, influenza virus, parainfluenza virus, herpes simplex virus, Zika virus, or Japanese encephalitis virus and other enveloped viruses.

BACKGROUND OF THE DISCLOSURE

Virus infections pose a major challenge for public health systems throughout the world. Despite rapid scientific progress in the field of virology, the lack of effective therapeutic options and vaccines for most viral infectious diseases continues to take its toll. Emerging viral diseases pose a major threat primarily because of their rapid transmission rates and the inherent difficulties associated with developing effective vaccines and treatment options against such novel pathogens in a short span of time. The SARS CoV-2 pandemic ongoing at the time of filing this application which has resulted in worldwide 31 million confirmed cases to date is a perfect example of such a major threat. Hence there is a need to develop broad-spectrum antiviral compounds that are effective against multiple viruses. Majority of currently available antivirals target one or more components directly associated with the virus life cycle. Hence the activity tends to be limited to closely related viruses, often within the same virus family. Select nucleoside analogues including cidofovir, favipiravir and ribavirin have shown to be effective against a broad range of viruses but pose a major risk of developing antiviral resistance mainly among RNA viruses. An ideal approach to circumvent such drawbacks associated with pathogen-specific antivirals is the use of host-targeting drugs, which both minimize the risk of virus-drug resistance and improves the spectrum of activity against multiple viruses across different virus families.

SUMMARY OF THE DISCLOSURE

The present disclosure provides a method for inhibiting entry of a virus into a host cell, comprising contacting the host cell with picolinic acid or a salt or derivative thereof. In some embodiments, the virus is an enveloped virus. In some embodiments, the virus is a syncytium-forming virus. In some embodiments, the virus is SARS-CoV-2, influenza, parainfluenza, herpes simplex virus (HSV), Japanese Encephalitis virus (JEV), Zika virus, or a flavivirus.

The present disclosure provides a method for treating or preventing a viral infection in a subject, comprising administering to the subject picolinic acid or a salt or derivative thereof. In some embodiments, the viral infection is caused by an enveloped virus. In some embodiments, the viral infection is caused by a syncytium-forming virus. In some embodiments, the viral infection is caused by SARS-CoV-2, parainfluenza, influenza, HSV, JEV, Zika virus, or a flavivirus.

The present disclosure provides picolinic acid or a salt or derivative thereof for use in inhibiting entry of a virus into a host cell. In some embodiments, the virus is an enveloped virus. In some embodiments, the virus is a syncytium-forming virus. In some embodiments, the virus is SARS-CoV-2, parainfluenza, influenza, HSV, JEV, Zika virus, or a flavivirus.

The present disclosure provides picolinic acid or a salt or derivative thereof for use as a medicament for treating or preventing a viral infection in a subject. In some embodiments, the viral infection is caused by an enveloped virus. In some embodiments, the viral infection is caused by a syncytium-forming virus. In some embodiments, the viral infection is caused by SARS-CoV-2, parainfluenza, influenza, HSV, JEV, Zika virus, or a flavivirus.

The present disclosure also provides compositions comprising picolinic acid or a salt or derivative thereof and a suitable excipient or carrier. In some embodiments, the present disclosure provides an oral, parenteral, intranasal, or inhalational pharmaceutical composition comprising picolinic acid or a salt or derivative thereof and a pharmaceutically acceptable excipient. In some embodiments, the present disclosure provides a dietary supplement comprising picolinic acid or a salt or derivative thereof and a suitable excipient or carrier. In some embodiments, the present disclosure provides a plant formulation comprising picolinic acid or a salt or derivative thereof and a suitable excipient or carrier.

BRIEF DESCRIPTION OF THE DRAWINGS

FIG. 1C shows a Western blot analysis of a cell lysate obtained from VeroE6 cells infected with Japanese Encephalitis Virus in the presence or absence of picolinic acid.

FIG. 2A shows results of an immunofluorescence assay of cells infected with influenza A virus in the presence or absence of picolinic acid at 3 hours post-infection.

Figure 1A:
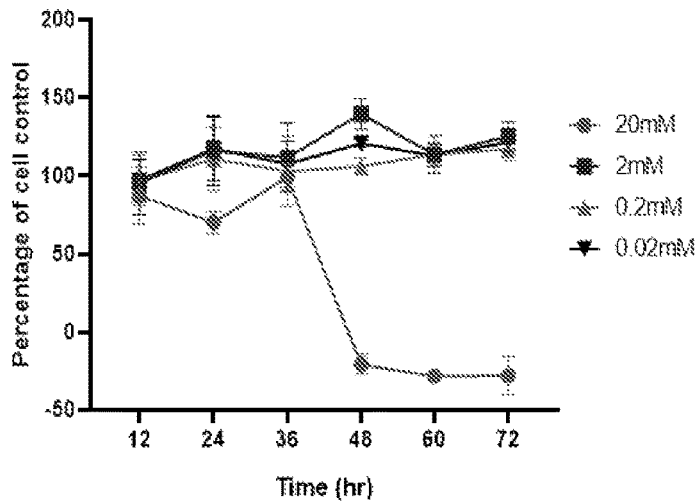
FIG. 1A shows results of a cell viability study using increasing concentration of picolinic acid.

"having", or "including but not limited to" wherever used, will be understood to imply the inclusion of a stated element, integer or step, or group of elements, integers or steps, but not the exclusion of any other element, integer or step, or group of elements, integers or steps.

Reference throughout this specification to "one embodiment", "an embodiment", or "some embodiments" means that a particular feature, structure or characteristic described in connection with the embodiment may be included in at least one embodiment of the present disclosure. Thus, the appearances of the phrases "in one embodiment", "in an embodiment", or "in some embodiments" in various places throughout this specification may not necessarily all refer to the same embodiment. It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination.

The term "subject" or "host" as used herein refers to a plant or an animal including humans, livestock animals, other primates (e.g., chimpanzees and other apes and monkey species), domestic mammals (e.g., dogs and cats), and laboratory animals (e.g., rodents such as mice, rats, and guinea pigs). The term "livestock' includes, but is not limited to, cattle (cows, buffaloes), horses, deer, sheep, goats, swine, poultry (including egg-producing poultry), elk, reindeer, bison, llamas, alpacas, fish, etc. In some embodiments, the subject or host is a mammal, bird, or a plant. In some embodiments, the subject is a human.

Picolinic acid (PA), also known as pyridine-2-carboxylic acid (IUPAC), is an endogenous metabolite of tryptophan in humans and is synthesized via the kynurenine pathway. It has been shown to exhibit various neuroprotective and anti-inflammatory effects in the body.

For any viral pathogen, infectious cycle begins with an entry into the host cell. For this step, many viruses exploit cellular endocytosis machinery or fuse at the cell membrane to deliver a viral genome inside the cells. The present inventors have found that picolinic acid interferes with and inhibits a virus entry into a host cell as well as early events associated with the virus entry for a range of viruses such as SARS-CoV-2, parainfluenza, influenza, HSV, Zika, and JEV. In particular, the present inventors have found that picolinic acid inhibits the viral entry at the step of endocytosis or membrane fusion. Since this is a shared step for a range of viral pathogens, picolinic acid can serve as a broad-spectrum antiviral compound for a range of viruses. Accordingly, the present disclosure provides methods for inhibiting a virus entry into a host cell and methods of treating and/or preventing viral infections in a subject by administering picolinic acid or a salt or derivative thereof.

In some embodiments, the present disclosure provides a method for inhibiting entry of a virus into a host cell, comprising contacting the host cell with picolinic acid or a salt or derivative thereof. In some embodiments, said contact is active (e.g., picolinic acid or a salt or derivative thereof is administered directly to target cells) or passive (e.g., picolinic acid or a salt or derivative thereof is administered to a subject and the administered compound reaches the target cell).

In some embodiments, the present disclosure provides a method for treating or preventing a viral infection in a subject, comprising administering to the subject picolinic acid or a salt or derivative thereof.

In some embodiments, the methods of the disclosure prevent entry of enveloped viruses into the host cell or treat and/or prevent infections caused by enveloped viruses. In some embodiments, the methods of the disclosure prevent entry of or treat or prevent infections caused by enveloped viruses having a single-stranded RNA genome into the host cell. In some embodiments, the methods of the disclosure prevent entry of or treat or prevent infections caused by enveloped viruses having a negative sense, single-stranded RNA genome into the host cell. In some embodiments, the methods of the disclosure prevent entry of or treat or prevent infections caused by enveloped viruses having a positive sense, single-stranded RNA genome into the host cell. In some embodiments, the methods of the disclosure prevent entry of or treat or prevent infections caused by enveloped viruses having a double-stranded DNA genome into the host cell. In some embodiments, the methods of the present disclosure are effective against enveloped viruses selected from the group consisting of SARS-CoV-2, parainfluenza, influenza, Japanese encephalitis virus (JEV), herpes simplex virus (HSV), Zika virus, or a flavivirus. In some embodiments, the methods of the disclosure prevent entry of syncytium-forming viruses into a host cell or treat or prevent infections caused by these viruses. The term "syncytium-forming" or "syncytia-forming" viruses as used herein refers to viruses that mediate fusion of an infected host cell with neighboring cells leading to the formation of multi-nucleate enlarged cells called syncytia. In some embodiments, the present methods are effective against syncytium-forming viruses which include, but are not limited to, viruses of family—Coronaviridae (e.g., SARS-CoV-2, MERS, SARS-CoV etc.), Herpesviridae (HSV, HCMV etc.), Paramyxoviridae (Nipah, Hendra, Measles, RSV etc.), Retroviridae (HIV, HTLV etc.), Hepatitis C Virus, Ebola, Sendai, Reovirus (e.g., Orthoreoviruses and Aquareoviruses).

The present disclosure encompasses all variants, strains, serotypes, wild-type, and mutant versions of the viruses disclosed herein.

In some embodiments, picolinic acid or a salt or derivative thereof is administered to the subject before entry of virus particles. In some embodiments, picolinic acid or a salt or derivative thereof is administered to the subject after entry of virus particles.

In some embodiments, the host cell is contacted with or the subject is administered with picolinic acid. In some other embodiments, the host cell is contacted with or the subject is administered with a salt or derivative of picolinic acid. In some embodiments, salts of picolinic acid include, but are not limited to, zinc picolinate, chromium picolinate, iron picolinate, sodium picolinate, and the like. In some embodiments, a derivative of picolinic acid is fusaric acid. In some embodiments, derivatives of picolinic acid include compounds synthesized by introducing substitutions at the 3, 4, 5 and/or 6 positions of picolinic acid.

Picolinic acid in moderate amounts is not cytotoxic to host cells; however, is effective in inhibiting entry of viruses into the host cells.

In some embodiments, administration of picolinic acid or a salt or derivative thereof to a subject inhibits entry of a virus into cells of the subject. Accordingly, in some embodiments, administration of picolinic acid or a salt or derivative thereof prevents the virus from establishing an active infection in the subject. The term "active infection" as used herein refers to a condition where the subject is exhibiting and/or suffering from symptoms of the infection. For example, in some embodiments, administration of picolinic acid or a salt or derivative thereof to a subject does not allow a build-up of viral titer in the subject, compared to a subject to whom picolinic acid or a salt or derivative thereof is not administered.

In embodiments where picolinic acid or a salt or derivative thereof is administered to a subject after entry of virus particles into cells of the subject, picolinic acid or a salt or derivative thereof inhibits entry of progeny virus particles into cells of the subject.

The terms "inhibits entry of a virus into cells of the subject" and "inhibits entry of a virus into a host cell" as used herein encompass inhibition of viral entry at the step of endocytosis or membrane fusion (syncytia formation) as well as other early events associated with entry of viruses into cells. Certain viruses enter a host cell via a process called receptor-mediated endocytosis. Some viruses enter the host cell via a direct membrane fusion where the envelope of the virus fuses with the cellular membrane. The present inventors found that picolinic acid inhibits both types of entry events, receptor-mediated endocytosis as well as viral-cellular membrane fusion. Further, after entry into the host cell, certain viruses induce fusion of infected host cell with neighboring cells—a process called syncytia-formation. The present inventors found that picolinic acid inhibits virus-induced syncytia formation. The present inventors also found that picolinic acid disrupts the integrity of viral envelope. Thus, picolinic acid exerts antiviral effects through inhibition of various early events associated with a virus entry into a host cell and can serve as a broad-spectrum inhibitor of viruses, particularly enveloped viruses and syncytium-forming viruses.

In some embodiments, administration of picolinic acid or a salt or derivative thereof to a subject reduces the viral titer in the subject. In some embodiments, the viral titer of the subject is reduced by about 10%, 15%, 20%, 25%, 30%, 35%, 40%, 45%, 50%, 55%, 60%, 65%, 70%, 75%, 80%, 85%, 90%, 95%, 99%, or almost about by 100%, compared to the viral titer prior to administration of picolinic acid or a salt or derivative thereof.

In some embodiments, upon administration of picolinic acid or a salt or derivative thereof, the viral titer of the subject is reduced by about 10-99%, 10-95%, 10-90%, 10-85%, 10-80%, 10-75%, 10-70%, 10-65%, 10-60%, 10-55%, 10-50%, 10-45%, 10-40%, 10-35%, 10-30%, 10-25%, 10-20%, 20-90%, 20-80%, 20-75%, 20-70%, 20-65%, 20-60%, 20-55%, 20-50%, 20-45%, 20-40%, 20-35%, 20-30%, 25-90%, 25-85%, 25-80%, 25-75%, 25-70%, 25-65%, 25-60%, 25-55%, 25-50%, 25-45%, 25-40%, 25-35%, 30-90%, 30-85%, 30-80%, 30-75%, 30-70%, 30-65%, 30-60%, 30-55%, 30-50%, 30-45%, 30-40%, 35-90%, 35-85%, 35-80%, 35-75%, 35-70%, 35-65%, 35-60%, 35-55%, 35-50%, 35-45%, 40-90%, 40-85%, 40-80%, 40-75%, 40-70%, 40-65%, 40-60%, 40-55%, 40-50%, 45-90%, 45-85%, 45-80%, 45-75%, 45-70%, 45-65%, 45-60%, 45-55%, 45-50%, 50-90%, 50-85%, 50-80%, 50-75%, 50-70%, 50-65%, 50-60%, 55-90%, 55-85%, 55-80%, 55-75%, 55-70%, 55-65%, 60-90%, 60-85%, 60-80%, 60-75%, 60-70%, 65-90%, 65-85%, 65-80%, 65-75%, 70-90%, 70-85%, 70-80%, 75-90%, 75-85%, or 80-90%, including values and ranges thereof, compared to the viral titer prior to administration of picolinic acid or a salt or derivative thereof.

In some embodiments, upon administration of picolinic acid or a salt or derivative thereof, the viral titer of the subject is reduced by about 25-90%, 25-75%, 25-60%, 25-50%, 30-90%, 30-70%, 30-60%, 40-90%, 40-80%, 40-75%, 40-70%, 40-60%, 50-90%, 50-80%, 50-75%, 60-90%, 60-80%, or 70-90%, including values and ranges thereof, compared to the viral titer prior to administration of picolinic acid or a salt or derivative thereof.

In some embodiments, administration of picolinic acid or a salt or derivative thereof to a subject reduces the viral titer of the subject by about 2.5-fold, 4-fold, 5-fold, 7-fold, 8-fold, 9-fold, 10-fold, 12-fold, 15-fold, 20-fold, 25-fold, 30-fold, 40-fold, or by about 50-fold, compared to the viral titer prior to administration of picolinic acid or a salt or derivative thereof. In some embodiments, administration of picolinic acid or a salt or derivative thereof to a subject reduces the viral titer of the subject by about 5-40 fold, 5-30 fold, 5-25 fold, 5-20 fold, 5-15 fold, 10-40 fold, 10-30 fold, 10-25 fold, or by about 10-20 fold, compared to the viral titer prior to administration of picolinic acid or a salt or derivative thereof.

In some embodiments, administration of picolinic acid or a salt or derivative thereof to a subject, suffering from an infection caused by SARS-CoV-2 virus, parainfluenza virus, influenza virus, HSV, JEV, Zika virus, or a flavivirus reduces titer of the respective virus in the subject by any of the values and ranges described herein.

In some embodiments, administration of picolinic acid or a salt or derivative thereof to a subject facilitates recovery of the subject from a viral infection compared to a subject not administered with picolinic acid or a salt or derivative thereof. For example, a subject administered with picolinic acid or a salt or derivative thereof experiences no or less loss of weight upon viral infection compared to a subject not administered with picolinic acid or a salt or derivative thereof.

In some embodiments, picolinic acid or a salt or derivative thereof is administered to a subject orally, parenterally, topically, intranasally, via inhalation, and/or via nebulization.

In some embodiments, picolinic acid or a salt or derivative thereof is administered orally. Oral administration comprises swallowing, so that picolinic acid or a salt or derivative enters the gastrointestinal tract, or buccal or sublingual administration by which picolinic acid or a salt or derivative enters the blood stream directly from the mouth. Accordingly, the present disclosure contemplates an oral pharmaceutical composition comprising picolinic acid or a salt or derivative thereof and a pharmaceutically acceptable excipient.

In some embodiments, picolinic acid or a salt or derivative is administered parenterally via injection or infusion. In parenteral administration, picolinic acid or a salt or derivative is administered directly into the blood stream or into muscles. Suitable means for parenteral administration include intravenous, intrathecal, intramuscular and subcutaneous. Suitable devices for parenteral administration include needle (including microneedle) injectors, needle-free injectors and infusion techniques. Accordingly, the present disclosure contemplates a parenteral pharmaceutical composition comprising picolinic acid or a salt or derivative thereof and a pharmaceutically acceptable excipient.

In some embodiments, picolinic acid or a salt or derivative thereof is formulated for topical administration to the skin or mucosa (i.e., dermally or transdermally) leading to systemic absorption of picolinic acid or a salt or derivative thereof. Accordingly, in some embodiments, provided herein is a topical pharmaceutical composition comprising picolinic acid or a salt or derivative thereof and a pharmaceutically acceptable excipient for preventing entry of a virus into the skin cells of a subject. In some embodiments, a topical formulation comprises picolinic acid or a salt or derivative thereof in an amount of about 5%, 10%, 15%, 20%, 25%, 30%, 35%, 40%, or about 50%, including values and ranges thereof, by weight of the formulation. In some embodiments, a topical formulation comprises picolinic acid or a salt or derivative thereof in an amount of about 5-50%, about 5-40%, about 5-30%, about 5-25%, about 5-20%, about 5-15%, about 10-50%, about 10-40%, about 10-30%, about 10-25%, about 10-20%, about 15-50%, about 15-40%, about 15-35%, about 15-30%, about 15-25%, about 20-50%, about 20-40%, about 20-30%, about 25-50%, about 25-40%, about 30-50%, about 30-45%, or about 40-50%, including values and ranges thereof, by weight of the formulation.

In some embodiments, picolinic acid or a salt or derivative is formulated for administration intranasally, by inhalation, or by nebulization. Accordingly, the present disclosure contemplates a pharmaceutical composition comprising picolinic acid or a salt or derivative thereof and a pharmaceutically acceptable excipient for intranasal or inhalational administration or administration by nebulization. In some embodiments, a composition for intranasal or inhalational administration or administration by nebulization comprises picolinic acid or a salt or derivative thereof at a concentration of about 0.01 mM to about 50 mM, about 0.01 mM to about 40 mM, about 0.01 mM to about 35 mM, 0.01 mM to about 30 mM, about 0.01 mM to about 25 mM, about 0.01 mM to about 20 mM, about 0.01 mM to about 15 mM, about 0.01 mM to about 10 mM, about 0.05 mM to about 50 mM, about 0.05 mM to about 45 mM, about 0.05 mM to about 40 mM, about 0.05 mM to about 35 mM, about 0.05 mM to about 30 mM, about 0.05 mM to about 25 mM, about 0.05 mM to about 20 mM, about 0.05 mM to about 15 mM, about 0.05 mM to about 10 mM, about 1 mM to about 50 mM, about 1 mM to about 40 mM, about 1 mM to about 35 mM, about 1 mM to about 30 mM, about 1 mM to about 25 mM, about 1 mM to about 20 mM, about 1 mM to about 15 mM, about 1 mM to about 10 mM, about 2.5 mM to about 50 mM, about 2.5 mM to about 40 mM, about 2.5 mM to about 35 mM, about 2.5 mM to about 30 mM, about 2.5 mM to about 25 mM, about 2.5 mM to about 20 mM, about 2.5 mM to about 15 mM, about 2.5 mM to about 10 mM, about 5 mM to about 50 mM, about 5 mM to about 45 mM, about 5 mM to about 40 mM, about 5 mM to about 35 mM, about 5 mM to about 30 mM, about 5 mM to about 30 mM, about 5 mM to about 25 mM, about 5 mM to about 20 mM, about 5 mM to about 15 mM, about 5 mM to about 10 mM, about 10 mM to about 50 mM, about 10 mM to about 45 mM, about 10 mM to about 40 mM, about 10 mM to about 35 mM, about 10 mM to about 30 mM, about 10 mM to about 25 mM, about 15 mM to about 50 mM, about 15 mM to about 45 mM, about 15 mM to about 40 mM, about 15 mM to about 30 mM, about 20 mM to about 50 mM, about 20 mM to about 45 mM, about 20 mM to about 40 mM, about 20 mM to about 30 mM, about 25 mM to about 50 mM, about 25 mM to about 45 mM, about 25 mM to about 40 mM, or about 30 mM to about 50 mM, including values and ranges thereof.

In some embodiments, a composition for intranasal or inhalational administration or administration by nebulization comprises picolinic acid or a salt or derivative thereof at a concentration of about 0.01 mM, 0.05 mM, 1 mM, 2.5 mM, 5 mM, 7.5 mM, 10 mM, 12.5 mM, 15 mM, 18 mM, 20 mM, 25 mM, 30 mM, 35 mM, 40 mM, or about 50 mM, including values and ranges therebetween.

The dosage regimen for picolinic acid or a salt or derivative thereof and/or compositions containing picolinic acid or a salt or derivative thereof is based on a variety of factors, such as, age, weight, sex and medical condition of the patient; and the route of administration. In some embodiments, systemic dosage for picolinic acid or a salt or derivative thereof can range from about 1 mg to about 100 mg, including values and ranges thereof, per kilogram of body weight per day. In some embodiments, systemic dosage for picolinic acid or a salt or derivative thereof can range from about 3 mg to about 100 mg, about 3 mg to about 90 mg, about 3 mg to about 80 mg, about 3 mg to about 75 mg, about 3 mg to about 70 mg, about 3 mg to about 60 mg, about 3 mg to about 50 mg, about 3 mg to about 45 mg, about 3 mg to about 40 mg, about 3 mg to about 30 mg, about 3 mg to about 25 mg, about 5 mg to about 100 mg, about 5 mg to about 90 mg, about 5 mg to about 80 mg, about 5 mg to about 75 mg, about 5 mg to about 70 mg, about 5 mg to about 60 mg, about 5 mg to about 50 mg, about 5 mg to about 45 mg, about 5 mg to about 40 mg, about 5 mg to about 30 mg, about 5 mg to about 25 mg, about 10 mg to about 100 mg, about 10 mg to about 90 mg, about 10 mg to about 80 mg, about 10 mg to about 75 mg, about 10 mg to about 70 mg, about 10 mg to about 60 mg, about 10 mg to about 50 mg, about 10 mg to about 45 mg, about 10 mg to about 40 mg, about 10 mg to about 30 mg, about 10 mg to about 25 mg, about 20 mg to about 100 mg, about 20 mg to about 90 mg, about 20 mg to about 80 mg, about 20 mg to about 75 mg, about 20 mg to about 70 mg, about 20 mg to about 60 mg, about 20 mg to about 50 mg, about 20 mg to about 40 mg, about 25 mg to about 100 mg, about 25 mg to about 90 mg, about 25 mg to about 80 mg, about 25 mg to about 75 mg, about 25 mg to about 70 mg, about 25 mg to about 60 mg, about 25 mg to about 50 mg, about 30 mg to about 100 mg, about 30 mg to about 90 mg, about 30 mg to about 80 mg, about 30 mg to about 75 mg, about 30 mg to about 70 mg, about 30 mg to about 60 mg, about 30 mg to about 50 mg, about 40 mg to about 100 mg, about 40 mg to about 90 mg, about 40 mg to about 80 mg, about 40 mg to about 75 mg, about 40 mg to about 70 mg, about 40 mg to about 60 mg, about 50 mg to about 100 mg, about 50 mg to about 90 mg, about 50 mg to about 80 mg, about 50 mg to about 75 mg, about 50 mg to about 70 mg, about 60 mg to about 100 mg, about 60 mg to about 90 mg, about 60 mg to 80 mg, about 70 mg to about 100 mg, about 70 mg to about 90 mg, or about 80 mg to about 100 mg, including values and ranges thereof, per kilogram of body weight per day. In some embodiments, a total daily dose for picolinic acid or a salt or derivative thereof is about 1 mg, 2 mg, 3 mg, 4 mg, 5 mg, 6 mg, 8 mg, 10 mg, 15 mg, 20 mg, 25 mg, 30 mg, 35 mg, 40 mg, 45 mg, 50 mg, 60 mg, 70 mg, 75 mg, 80 mg, 90 mg, or about 100 mg, including values and ranges thereof, per kilogram of body weight.

In some embodiments, total daily dose for picolinic acid or a salt or derivative thereof can range from about 200 mg to about 2000 mg, about 200 mg to about 1800 mg, about 200 mg to about 1600 mg, about 200 mg to about 1500 mg, about 200 mg to about 1400 mg, about 200 mg to about 1200 mg, about 200 mg to about 1000 mg, about 200 mg to about 800 mg, about 200 mg to about 700 mg, about 200 mg to about 600 mg, about 200 mg to about 500 mg, about 200 mg to about 400 mg, about 300 mg to about 2000 mg, about 300 mg to about 1800 mg, about 300 mg to about 1600 mg, about 300 mg to about 1400 mg, about 300 mg to about 1200 mg, about 300 mg to about 1000 mg, about 300 mg to about 800 mg, about 300 mg to about 600 mg, about 400 mg to about 2000 mg, about 400 mg to about 1800 mg, about 400 mg to about 1600 mg, about 400 mg to about 1500 mg, about 400 mg to about 1400 mg, about 400 mg to about 1200 mg, about 400 mg to about 1000 mg, about 400 mg to about 800 mg, about 400 mg to about 700 mg, about 500 mg to about 2000 mg, about 500 mg to about 1800 mg, about 500 mg to about 1600 mg, about 500 mg to about 1500 mg, about 400 mg to about 1400 mg, about 400 mg to about 1200 mg, about 400 mg to about 1000 mg, about 400 mg to about 800 mg, about 500 mg to about 2000 mg, about 500 mg to about 1800 mg, about 500 mg to about 1600 mg, about 500 mg to about 1500 mg, about 500 mg to about 1400 mg, about 500 mg to about 1200 mg, about 500 mg to about 1000 mg, about 500 mg to about 800 mg, about 600 mg to about 2000 mg, about 600 mg to about 1800 mg, about 600 mg to about 1600 mg, about 600 mg to about 1500 mg, about 600 mg to about 1400 mg, about 600 mg to about 1200 mg, about 600 mg to about 1000 mg, about 700 mg to about 2000 mg, about 700 mg to about 1800 mg, about 700 mg to about 1600 mg, about 700 mg to about 1500 mg, about 700 mg to about 1400 mg, about 700 mg to about 1200 mg, about 700 mg to about 1000 mg, about 800 mg to about 2000 mg, about 800 mg to about 1800 mg, about 800 mg to about 1600 mg, about 800 mg to about 1500 mg, about 800 mg to about 1400 mg, about 800 mg to about 1200 mg, about 1000 mg to about 2000 mg, about 1000 mg to about 1800 mg, about 1000 mg to about 1500 mg, about 1200 mg to about 2000 mg, about 1200 mg to about 1800 mg, about 1400 mg to about 2000 mg, about 1500 mg to about 2000 mg, including values and ranges thereof, per kilogram of body weight per day. In some embodiments, a total daily dose for picolinic acid or a salt or derivative thereof is about 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, or about 2000 mg, including values and ranges thereof, per kilogram of body weight.

The total daily dose can be administered once or a plurality of times in a day. In some embodiments, the total daily dose is administered orally or parenterally.

For oral administration, picolinic acid or a salt or derivative thereof may be provided in the form of an oral dosage form containing 1, 2.5, 5, 10, 15, 20, 25, 30, 50, 75, 100, 125, 150, 200, 250, 300, 400 and 500 milligrams of picolinic acid or a salt or derivative thereof. Oral dosage forms containing picolinic acid or a salt or derivative thereof can be discrete units, such as hard or soft capsules, tablets, pills, or lozenges; or in a liquid form such as emulsions, solutions, suspensions, syrups, and elixirs.

For parenteral administration, e.g., intravenous administration, picolinic acid or a salt or derivative thereof may be administered in an amount of about 0.1 to 10 mg/kg/minute. For parenteral administration, a parenteral dose form containing desired amount of picolinic acid or a salt or derivative thereof may be formulated.

For intranasal administration, administration by inhalation, or administration by nebulization, picolinic acid or a salt or derivative thereof can be delivered in the form of a solution, suspension or aerosol.

In some embodiments, picolinic acid or a salt or derivative thereof may be provided in the form of a dietary supplement containing about 10, 15, 20, 25, 30, 40, 50, 60, 70, 75, 80, 90, 100, 125, 150, 200, 250, 300, 400 and 500 milligrams of picolinic acid or a salt or derivative thereof. Said dietary supplement can contain one or more carriers suitable for oral ingestion. A dietary supplement composition can be in the form of a powder, liquid, solution, suspension, pill, capsule, tablet, gel cap, gel, nutrition bars, etc.

In some embodiments, the present disclosure provides use of picolinic acid or a salt or derivative thereof for inhibiting entry of a virus into a host cell. In some embodiments, the virus is SARS-CoV-2, influenza, parainfluenza, HSV, JEV, Zika virus, or a flavivirus and the host cell is a mammalian cell, an avian cell or a plant cell.

In some embodiments, the present disclosure provides picolinic acid or a salt or derivative thereof for use as a medicament for treating or preventing a viral infection in a subject. In some embodiments, the viral infection is a SARS-CoV-2, influenza, parainfluenza, HSV, JEV, Zika virus, or a flavivirus infection. Dosage forms, dosages, and routes of administration that may be employed for the medicament are discussed above.

In some embodiments, the present disclosure provides a method for treating a plant viral infection comprising applying to the plant or contacting the plant cell with picolinic acid or a salt or derivative thereof. In some embodiments, plant viruses that can be treated by application of picolinic acid or a salt or derivative thereof include, but are not limited to, viruses of family Geminiviridae (e.g., Cassava Mosaic Virus, Maize streak virus); Caulimoviridae (e.g., Banana streak virus, Rice Tungro Bacilliform virus); Potyviridae (e.g., Sugarcane mosaic virus, Maize dwarf mosaic virus, Sweet potato feathery mottle virus); Tombusviridae (e.g., Barley yellow dwarf viruses); Bromoviridae (e.g., Cucumber mosaic virus); and Nanoviridae (e.g., Banana bunchy top virus).

In some embodiments, the present disclosure provides a horticultural, arboricultural, or agricultural composition (collectively referred to herein as a "plant formulation") where picolinic acid or a salt or derivative is formulated for application to plants for treating plant viral infections. In some embodiments, the plant formulation is a liquid formulation such as a solution or suspension that can be manually applied to plants or sprayed on plants. In some embodiments, the plant formulation is an aerosol formulation that is sprayed on plants. In some embodiments, the plant formulation is a dry formulation such as granules, powder, etc. that is added to soil. In some embodiments, the plant formulation is a spray formulation that is a liquid or aerosol that can be sprayed on plants. The amount of picolinic acid or a salt or derivative thereof in the plant formulation can range from about 10% to about 95%, including values and ranges thereof, by weight of the formulation depending on the type of formulation and the place of application (leaves, stem, soil, etc).

In some embodiments, the amount of picolinic acid or a salt or derivative thereof in the plant formulation ranges from about 10-95%, 10-90%, 10-85%, 10-80%, 10-75%, 10-70%, 10-65%, 10-60%, 10-55%, 10-50%, 10-45%, 10-40%, 10-35%, 10-30%, 10-25%, 10-20%, 20-90%, 20-80%, 20-75%, 20-70%, 20-65%, 20-60%, 20-55%, 20-50%, 20-45%, 20-40%, 20-35%, 20-30%, 25-90%, 25-85%, 25-80%, 25-75%, 25-70%, 25-65%, 25-60%, 25-55%, 25-50%, 25-45%, 25-40%, 25-35%, 30-90%, 30-85%, 30-80%, 30-75%, 30-70%, 30-65%, 30-60%, 30-55%, 30-50%, 30-45%, 30-40%, 35-90%, 35-85%, 35-80%, 35-75%, 35-70%, 35-65%, 35-60%, 35-55%, 35-50%, 35-45%, 40-90%, 40-85%, 40-80%, 40-75%, 40-70%, 40-65%, 40-60%, 40-55%, 40-50%, 45-90%, 45-85%, 45-80%, 45-75%, 45-70%, 45-65%, 45-60%, 45-55%, 45-50%, 50-90%, 50-85%, 50-80%, 50-75%, 50-70%, 50-65%, 50-60%, 55-90%, 55-85%, 55-80%, 55-75%, 55-70%, 55-65%, 60-90%, 60-85%, 60-80%, 60-75%, 60-70%, 65-90%, 65-85%, 65-80%, 65-75%, 70-90%, 70-85%, 70-80%, 75-90%, 75-85%, or 80-90%, including values and ranges thereof, by weight of the formulation.

The plant formulations comprise one or more horticulturally or agriculturally suitable excipients. In some embodiments, the plant formulations comprise solvents such as water or a mixture of water with an organic solvent; surfactants; humectants, etc.

It is to be understood that the foregoing descriptive matter is illustrative of the disclosure and not a limitation. While considerable emphasis has been placed herein on the particular features of this disclosure, it will be appreciated that various modifications can be made, and that many changes can be made in the preferred embodiments without departing from the principles of the disclosure. Those skilled in the art will recognize that the embodiments herein can be practiced with modification within the spirit and scope of the embodiments as described herein. Similarly, additional embodiments and features of the present disclosure will be apparent to one of ordinary skill in art based upon description provided herein.

Descriptions of well-known/conventional methods/steps and techniques are omitted so as to not unnecessarily obscure the embodiments herein. Further, the disclosure herein provides for examples illustrating the above-described embodiments, and in order to illustrate the embodiments of the present disclosure certain aspects have been employed. The examples used herein for such illustration are intended merely to facilitate an understanding of ways in which the embodiments herein may be practiced and to further enable those of skill in the art to practice the embodiments herein. Accordingly, the following examples should not be construed as limiting the scope of the embodiments herein.

EXAMPLES

Example 1

Picolinic Acid Inhibits Replication of Human Parainfluenza, Herpes, and Influenza Virus Cytotoxicity of picolinic acid (PA) was tested by incubating human lung epithelial cells (A549 cells) with increasing concentrations of PA for up to 72 hrs and cell viability was measured at every 12 hr time intervals using Alamar Blue cell viability reagent (FIG. 1A). A549 cells were procured from ATCC, Manassas, Va., USA.

Drug concentration up to 2 mM PA was shown to be non-toxic to cells over the period of 72 hr tested. The highest concentration of 20 mM resulted in loss of cell viability 36 hr post treatment. Based on these results, a working concentration of 2 mM or below was used for all subsequent experiments.

Figure 1B:
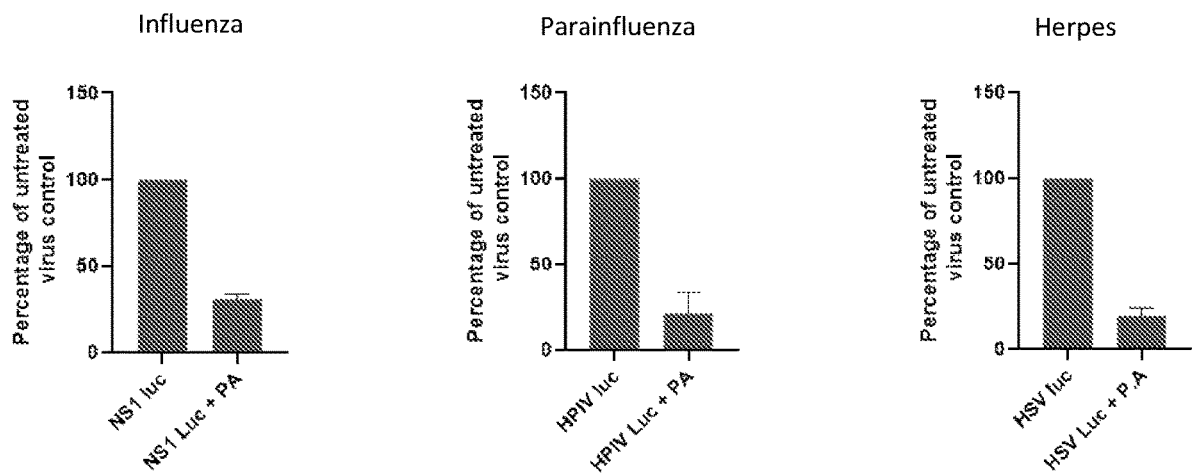
FIG. 1B shows results of the luminescence assay for cells infected with firefly luciferase expressing influenza A virus, parainfluenza virus, and HSV-1 virus in the presence or absence of picolinic acid.

A549 cells were pre-treated with 2 mM PA for 3 hrs, washed and infected with firefly luciferase expressing Influenza virus (NS1 Luc), Para Influenza virus (HPIV Luc), and Herpes Simplex virus 1 (HSV1 Luc) either in the presence of PA. A second set of A549 cells was not pre-treated with PA (untreated) and was infected with the above-mentioned firefly luciferase viral constructs in the absence of PA. This set served as untreated virus control. Luminescence assay was performed 48 hr post infection, using Promega firefly luciferase assay system and results were plotted against percentage of untreated virus control (FIG. 1B). The cells pre-treated with 2 mM PA showed 70-80% inhibition of the three different viruses tested.

Figures 1C, 2A:
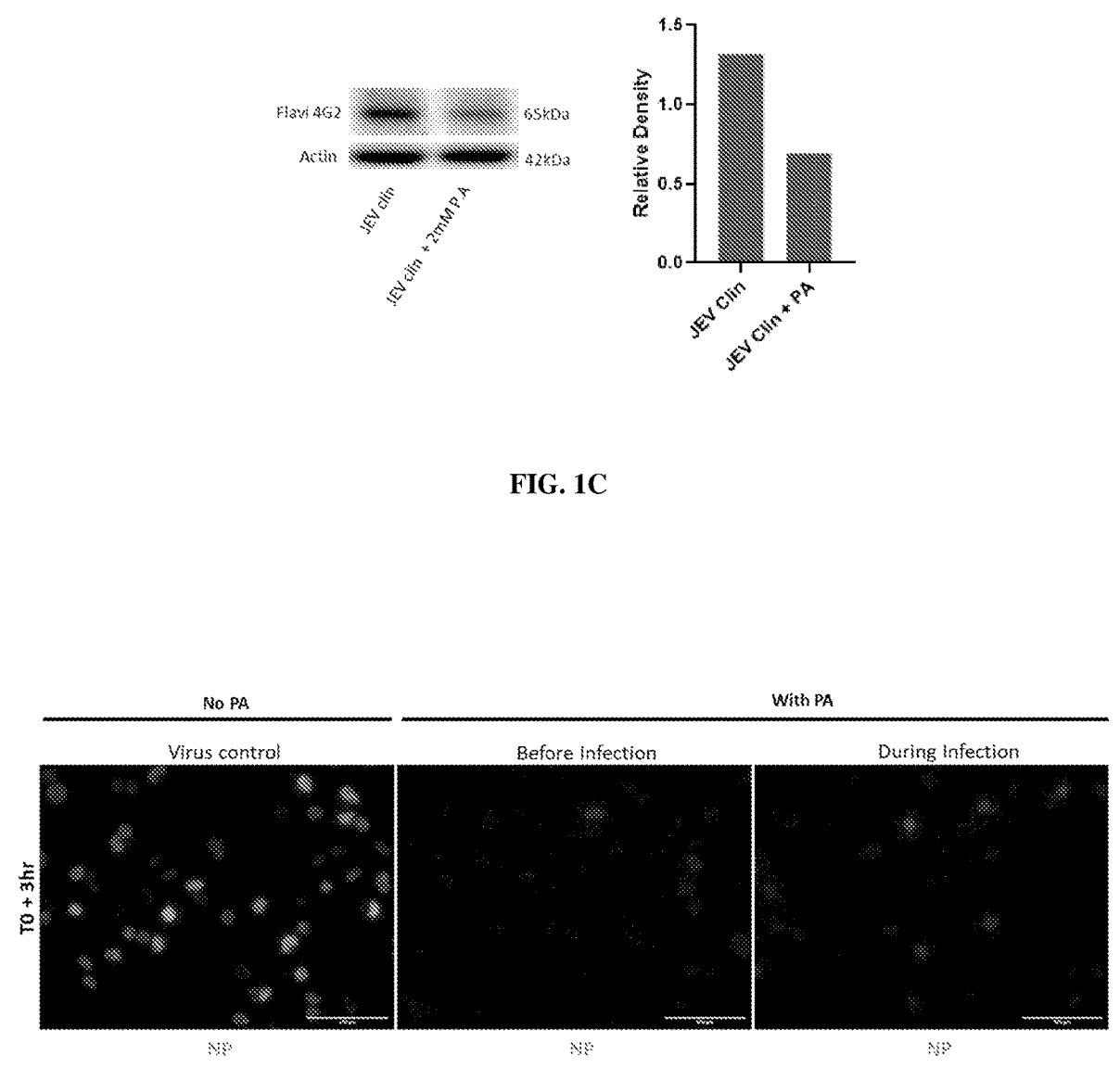

VeroE6 cells (procured from ATCC, Manassas, Va., USA) were pre-treated with 2 mM PA, washed, and infected with Japanese Encephalitis Virus (JEV) clinical strain P20778 in the presence of PA. A second set of VeroE6 cells was not pre-treated with PA (untreated) and was infected with JEV P20778 in the absence of PA. This set served as untreated virus control. Cells were lysed 48 hr post infection, cell lysates were prepared followed by the western blot analysis. Virus envelope protein expression levels were detected using anti-Flavivirus 4G2 antibody. A relative density of the bands was normalized against actin loading control and plotted using GraphPad Prism (FIG. 1C). A 0.75-fold decrease in the flavivirus envelope protein expression was evident from western blot analysis of JEV infected cells, treated with PA.

These results indicate a broad-spectrum activity of PA across both DNA (HSV) and RNA (influenza A virus, parainfluenza virus, and JEV) viruses belonging to three different families.

Example 2

Picolinic Acid Inhibits Influenza A Virus Entry

In this experiment, cells were divided into four groups: (i) Untreated Control: cells were not treated with PA at any time during the experiment; (ii) Before Infection: cells were pre-treated with 2 mM PA for 3 hr and infected with the virus in the presence of PA; (iii) During Infection: cells were infected with the virus in the presence of PA; and (iv) After Infection: cells were infected with the virus and 3 hrs later treated with PA. This is discussed in more details below.

Figure 2B:
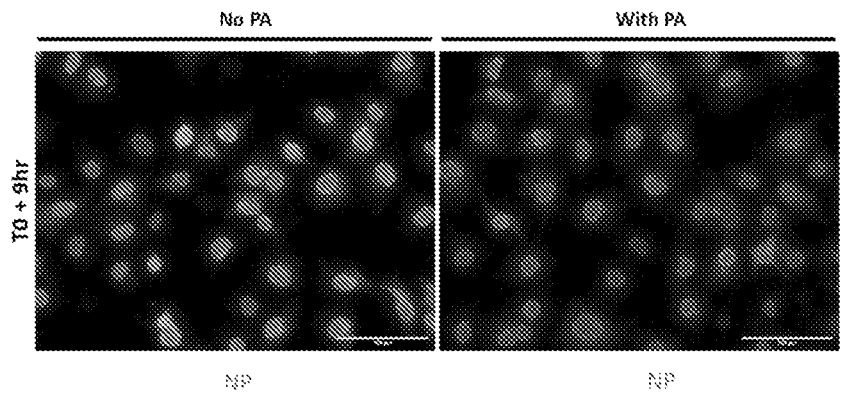
FIG. 2B shows results of an immunofluorescence assay of cells infected with influenza A virus in the presence or absence of picolinic acid at 9 hours post-infection.

A549 cells were pre-treated with 2 mM PA for 3 hr (Before Infection), washed and infected (T0) with PR8 WT virus (strain A/Puerto Rico/8/1934 H1N1) at 2 multiplicity of infection (MOI) in the presence of 2 mM PA. After 3 hr infection (T0+3 hr), the cells were fixed with 4% formalin, permeabilized and used for immunofluorescence assay. See FIG. 2A, "Before Infection".

A mixture of 2 MOI PR8 WT and 2 mM PA was made in 1.5 tubes (During Infection), incubated at 37° C. for 1 hr and used to infect cells. Cells were fixed 3 hr post infection and used for immunofluorescence assay. See FIG. 2A, "During Infection".

Cells were infected with 2 MOI PR8 WT virus, 3 hr later (After infection) treated with 2 mm PA and fixed after a further incubation period of 6 hr (T0+9 hr). See FIG. 2B.

Immunolabelling of virus infected cells was done using mouse anti-Influenza virus nucleoprotein (NP) antibody, followed by detection with Alexa Fluor 488 labelled anti-mouse secondary antibody.

Figure 2C:
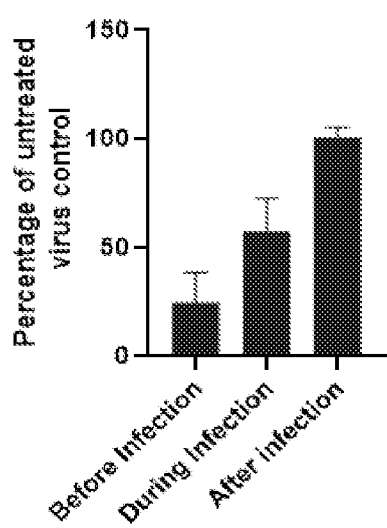
FIG. 2C shows a graph of a total number of nucleoprotein (NP) positive cells against untreated virus control for three different conditions.

Total number of NP positive cells was quantified using ImageJ/Fiji from 6 different microscopic fields per experimental condition. The results were plotted against percentage of untreated virus control using GraphPad Prism. See FIG. 2C.

Figure 2D:
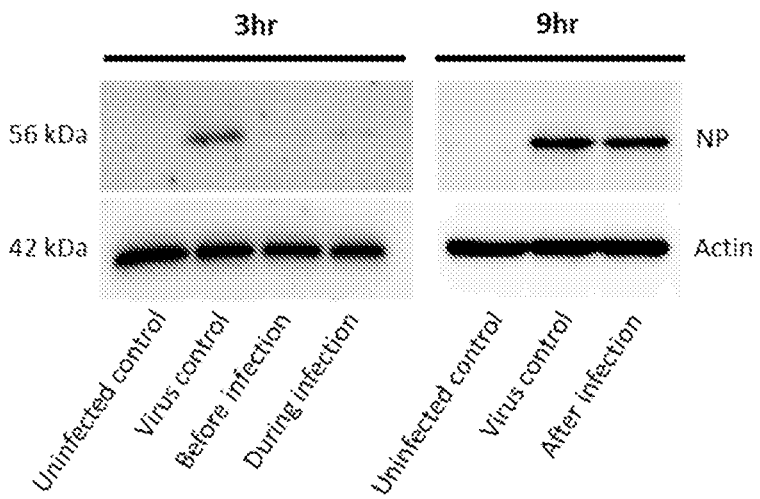
FIG. 2D shows a Western blot analysis of cell lysates obtained from three different conditions for the expression of influenza A virus NP.

Western Blot analysis was performed for lysates collected from different conditions as indicated, and virus protein expression was detected using mouse anti-Influenza virus NP antibody. See FIG. 2D.

A 75% decrease in number of NP positive cells compared to virus control was observed when cells were pre-treated with 2 mm PA (Before Infection) and there was only a 40% decrease when cells were infected with virus and drug mixture (During Infection). A similar trend was observed in western blot analysis as well. However, no decrease in NP positive cells was observed when cells were treated 3 hr post infection (After Infection). Similarly, no difference was observed between expression levels of virus NP in virus control and PA treated cells by western blot.

Results from both immunofluorescence and western blot assays showed the anti-viral activity of PA when cells were pre-treated with PA. This indicates that PA interferes with the virus entry or early steps associated with the virus entry. PA did not show anti-viral activity when cells were treated with PA after infection, implying that virus entry has already occurred during this time and that PA did not inhibit late events in virus replication. Although PA did not inhibit late events in virus replication, PA will inhibit entry of progeny virus, generated from virus replication, into host cells.

Example 3

Figure 3A:
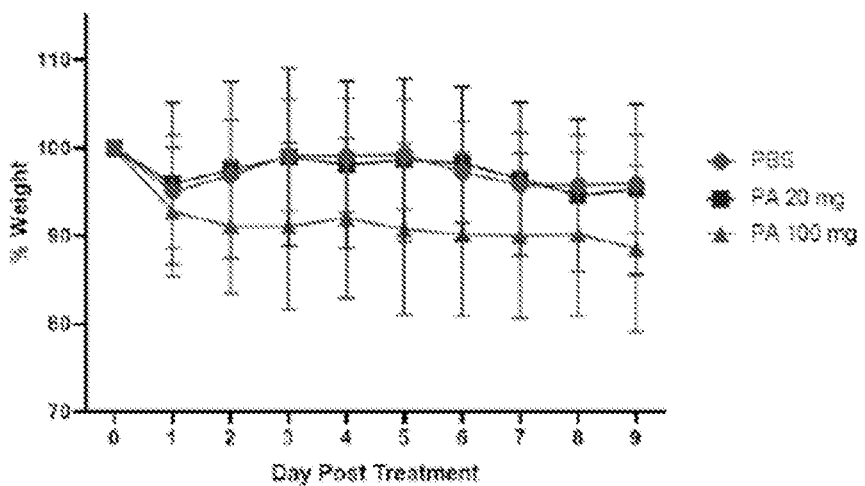
FIG. 3A shows percent weight loss in mice upon treatment of mice with 20 or 100 mg of picolinic acid.

Picolinic Acid Inhibits Influenza A Virus (IAV) Induced Disease in Mice at a Non-Toxic Dose Healthy 4-6 weeks old female BALB/c mice (procured from the Central Animal Facility at Indian Institute of Science, Bengaluru) were treated (N=5 per group) with 20 or 100 mg PA by intraperitoneal route. One group served as PBS (untreated) control. The body weight of animals was measured every day for up to 9 days post treatment and percentage differences in body weight was plotted. See FIG. 3A. Drug toxicity results showed a gradual 10-12% decrease in total body weight of animals treated with 100 mg PA. However, there were no differences in body weight of animals treated with 20 mg PA and this was similar to that of PBS treated control animals.

Figure 3B:
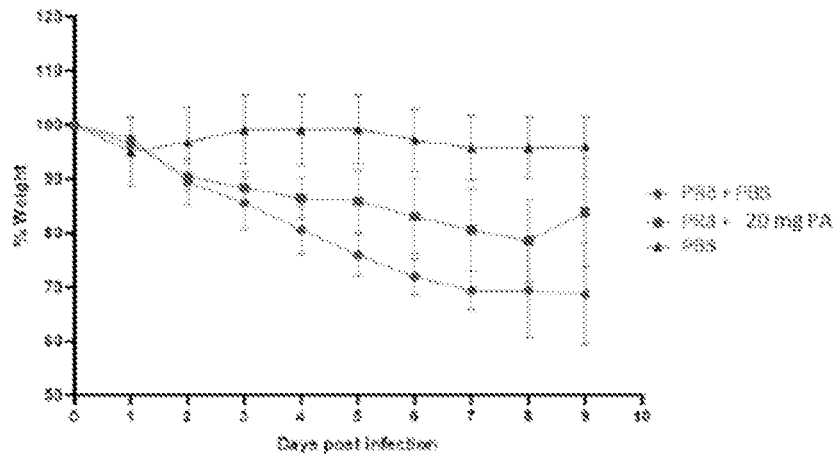
FIG. 3B shows percent weight loss in mice infected with influenza A virus and pre-treated with picolinic acid and vehicle-treated mice.

Test group of mice were treated with 20 mg PA for 6 hr and then infected with IAV PR8 WT strain via intra nasal route (N=5 per group). Control group of mice did not receive PA. Animals inoculated with PBS alone served as the non-infected control. The body weights of animals were then monitored over a period of 9 days and percentage differences in body weight was plotted using GraphPad Prism. See FIG. 3B. Animals infected with PR WT in the presence of 20 mg PA showed minimal loss in body weight followed by a recovery phase after 8 days infection. This was in contrast to the 30% body weight loss that was observed in the case of animals infected in the presence of 100 mg PA.

A working concentration of 20 mg PA was chosen based on the toxicity study and this concentration was shown to rescue animals from PR8 WT virus infection, as evidenced by reduced body weight loss in the presence of the drug. The results correlate with in vitro data performed in A549 cells shown in FIG. 1A, wherein nontoxic dose of PA was shown to inhibit virus replication.

Example 4

Figure 4A:
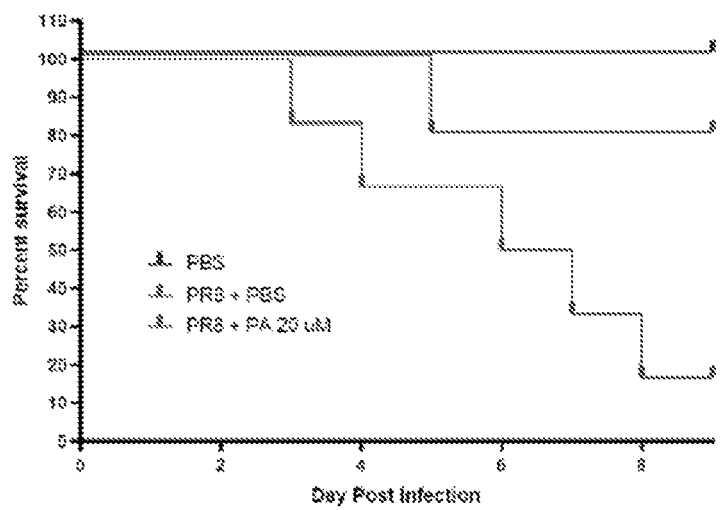
FIG. 4A shows survival rate of mice infected with influenza A virus and pre-treated with picolinic acid and vehicle-treated mice.

Picolinic Acid Inhibits IAV Replication and Pathology in Mice at a Non-Toxic Dose Healthy 4-6 weeks old female BALB/c mice (procured from the Central Animal Facility at Indian Institute of Science, Bengaluru) were treated with 20 mg PA for 6 hr and then infected with IAV PR8 WT strain via intra nasal route (N=5 per group). Control group of mice did not receive any PA. Animals inoculated with PBS alone served as the noninfected control. The survival rate of animals was then monitored for up to 9 days and plotted. See FIG. 4A. Beginning at 3 days post infection, a steady decrease in survival rate of control animals without PA treatment was observed, resulting in over 80% decrease in percentage survival after 9 days. This effect was significantly reduced in animals treated with 20 mg PA.

Figure 4B:
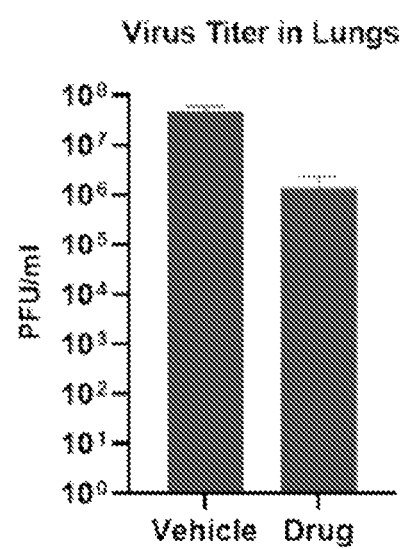
FIG. 4B shows viral tire in mice pre-treated with picolinic acid and vehicle-treated mice.

Mice from both control and drug treated groups were sacrificed 72 hr post infection and total lung tissue was recovered and homogenized. Virus titre from the tissue homogenate was then measured using influenza virus plaque assay in MDCK cells and results plotted using GraphPad Prism. See FIG. 4B. Over 10-fold decrease in virus titre from lung tissue samples was evident in infected animals treated with PA compared to untreated.

The rescue of PA treated animals from IAV induced death correlates well with the previously observed results of reduced body weight loss. Reduction of lung virus titre in PA treated animals is a clear indication of antiviral effects in vivo.

Example 5

Picolinic Acid Inhibits SARS-CoV-2 Entry in Pseudotyped Particle Assay

Figure 5A:
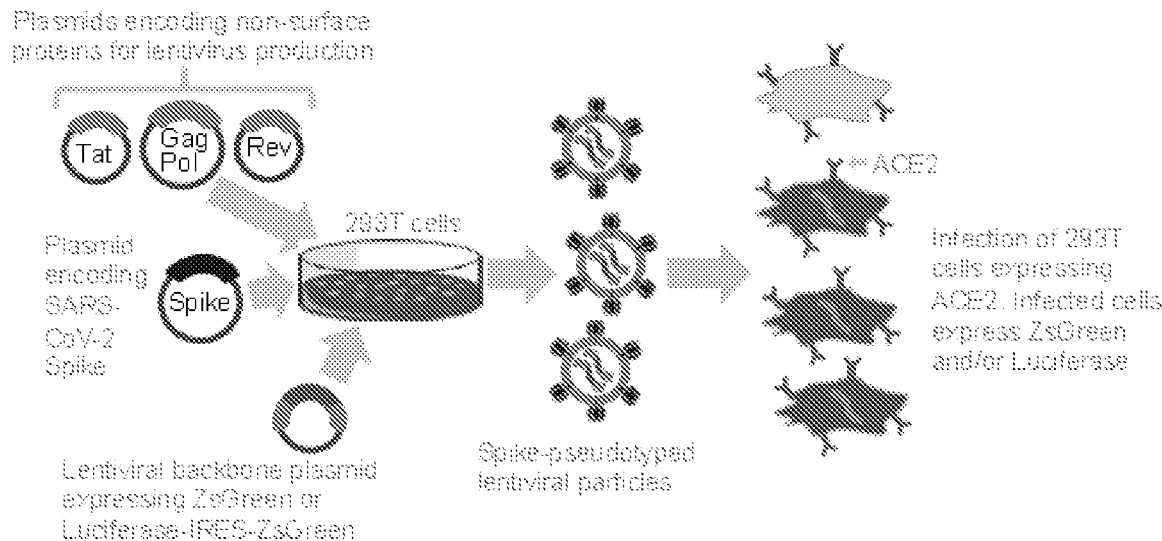
FIG. 5A shows different steps involved in the production of pseudotyped SARS CoV-2 particles.

FIG. 5A shows a schematic illustrating different steps involved in the production of pseudotyped SARS CoV-2 particles. This schematic is sourced from Viruses 2020, 12(5), 513; www.doi.org/10.3390/v12050513.293T cells were transfected with plasmids encoding a lentiviral backbone (genome) expressing a marker protein, SARS CoV-2 spike, and other HIV proteins needed for virion formation (Tat, Gag-Pol, and Rev). After 60 hr, the pseudotyped particles were collected and used for infection of cells expressing ACE2 receptor.

Figure 5B:
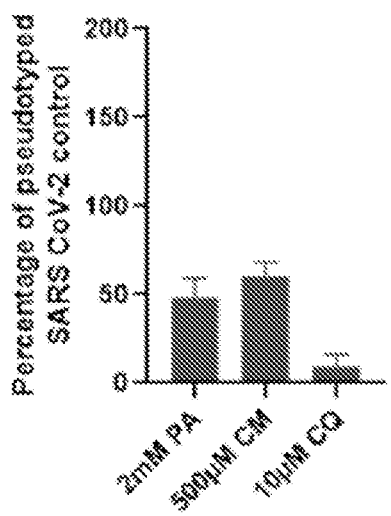
FIG. 5B shows results of a luminescence assay of cells infected with pseudotyped SARS CoV-2 particles in presence of picolinic acid, chloroquine (CQ), and camostat mesylate (CM).

HEK ACE2 cells (procured from BEI Resources, Manassas, Va., USA) in a 96 well plate were pre-treated for 3 hr with 2 mM PA, 10 μM Chloroquine (CQ) or 500 μM Camostat mesylate (CM) individually, washed and infected with pseudotyped SARS CoV-2 particles in the presence or absence of respective drugs. Firefly (Luc2) luminescence readings were measured 72 hr post infection and results were plotted against percentage of untreated virus control using GraphPad prism. See FIG. 5B. Over 50% inhibition of pseudotyped SARS CoV-2 virus entry was observed in the presence of 2 mM PA, compared to 60 and 90% inhibition that was observed with CM and CQ, respectively.

The results indicate that PA treatment of cells inhibited pseudotyped SARS CoV-2 virus entry at an IC50 of 2 mM and this was almost 10% more effective than CM, an inhibitor of the cellular enzyme transmembrane protease serine 2 (TMPRSS2).

Example 6

Picolinic Acid Inhibits SARS-CoV-2 Replication in Different Cell Lines

VeroE6 (procured from ATCC, Manassas, Va., USA), HEK ACE2 (procured from BEI Resources, Manassas, Va., USA) and Calu3 cells (procured from ATCC, Manassas, Va., USA) were seeded in 24 well cell culture plates. The cells were pre-treated for 3 hr with 2 mM PA, washed and infected with 0.01 MOI SARS-CoV-2 (isolate hCoV-19/Hong Kong/VM20001061/2020 procured from BEI Resources, Manassas, Va., USA) in the presence of PA. A control set of cells for each cell line was not pre-treated with PA and was infected with the SARS-CoV-2 virus strain in the absence of PA. After 48 hr infection, the cells were washed, and total RNA was isolated using Trizol. Viral RNA load was determined by RT-qPCR and results were plotted against $\log_{10}$ copy number of viral RNA.

Figure 6:
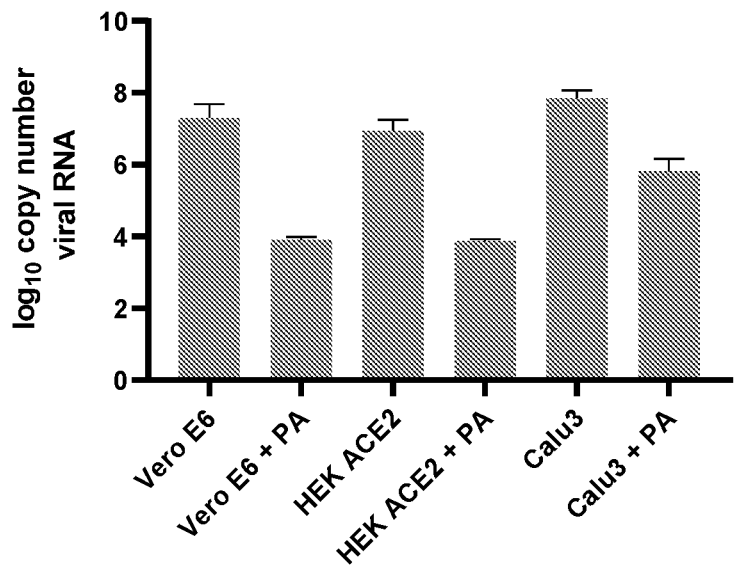
FIG. 6 shows results of a qRT-PCR assay showing viral RNA load in three different cells infected with SARS-CoV-2 in the presence of absence of picolinic acid.
Figure 7A:
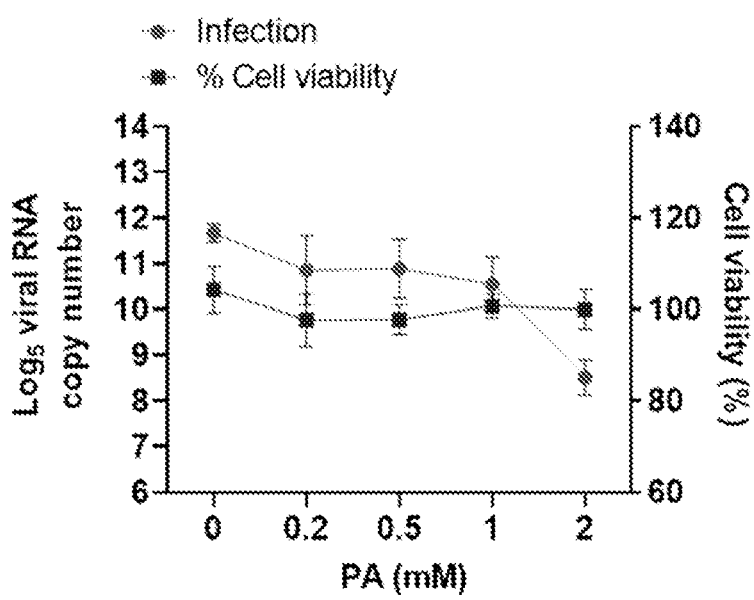
FIG. 7A shows results of a qRT-PCR assay showing viral RNA copy numbers in HEK ACE2 cells pre-treated for 3 hr with increasing doses of PA as indicated and infected with 0.1 MOI of SARS-CoV-2 Hong Kong.
Figure 7B:
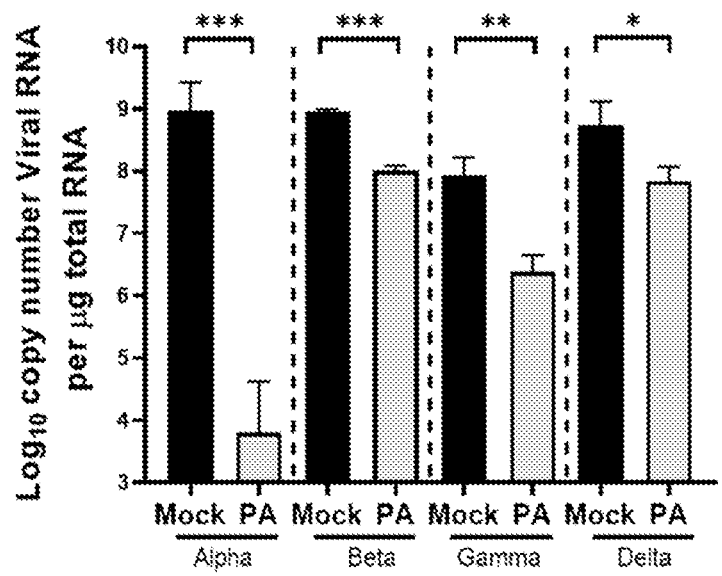
FIG. 7B shows results of a qRT-PCR assay showing viral RNA copy numbers in HEK ACE2 cells pre-treated for 3 hr with 2 mM PA and infected with 0.1 MOI of four SARS-CoV-2 variants of concern.
Figure 7C:
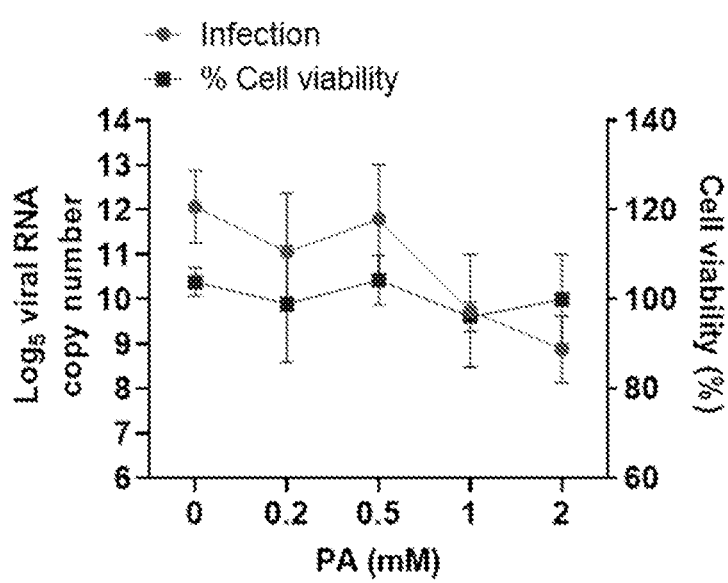
FIG. 7C shows results of a qRT-PCR assay showing viral RNA copy numbers in VeroE6 cells pre-treated for 3 hr with increasing doses of PA as indicated and infected with 0.001 MOI of SARS-CoV-2 Hong Kong.
Figure 7D:
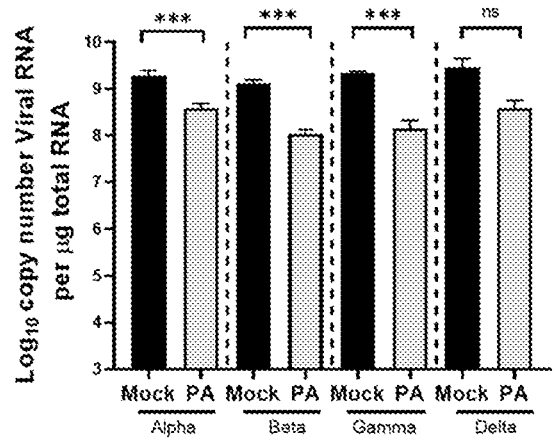
FIG. 7D shows results of a qRT-PCR assay showing viral RNA copy numbers in VeroE6 cells pre-treated for 3 hr with 2 mM PA and infected with 0.001 MOI of four SARS-CoV-2 variants of concern.
Figure 7E:
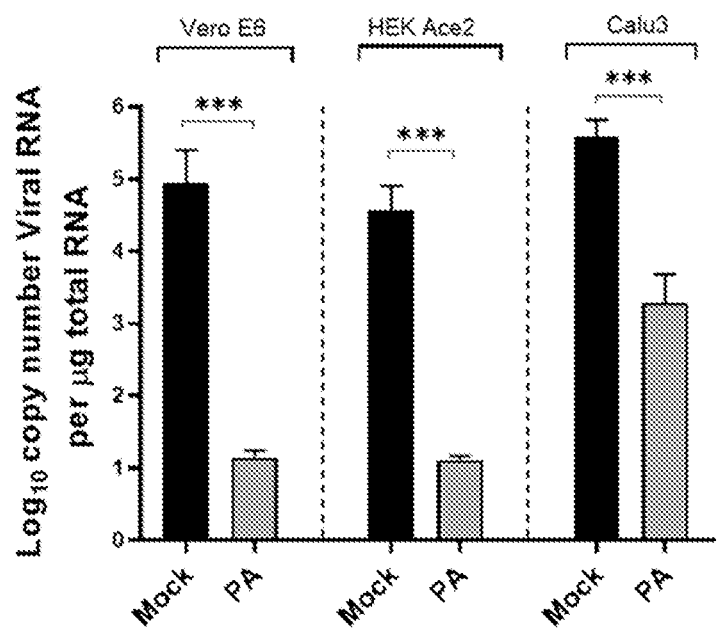
FIG. 7E shows results of a qRT-PCR assay showing viral RNA copy numbers in VeroE6, HEK ACE2 and Calu3 cells pre-treated with 2 mM PA and infected with 0.1 MOI SARS-CoV-2 for 48 hr.
Figure 7F:
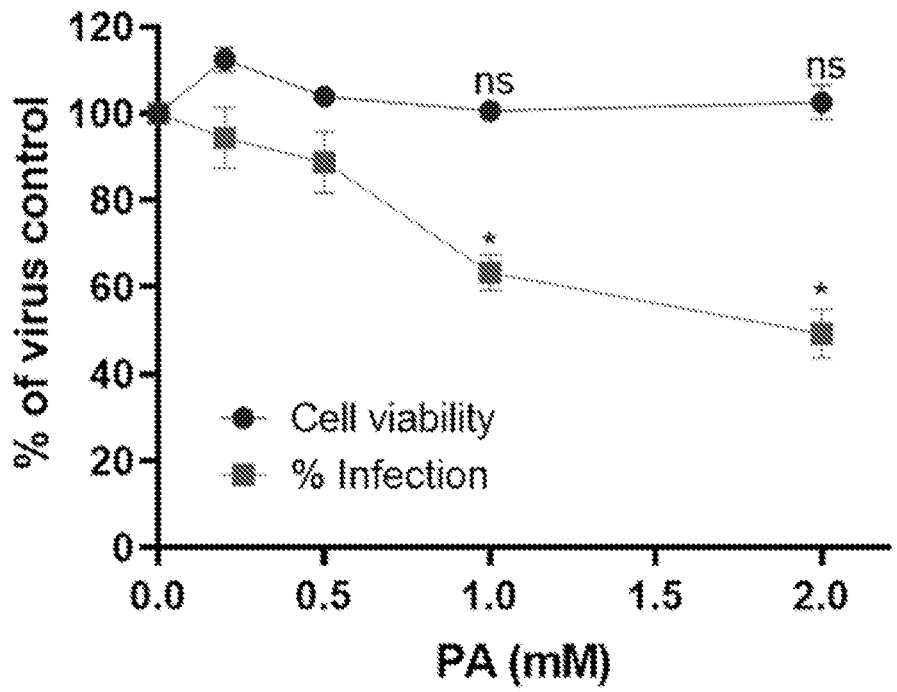
FIG. 7F shows results of a plaque assay of supernatants of MDCK cells pre-treated with increasing concentrations of PA and infected with 0.01 MOI of PR8 wild type virus for 48 hr.
Figure 7G:
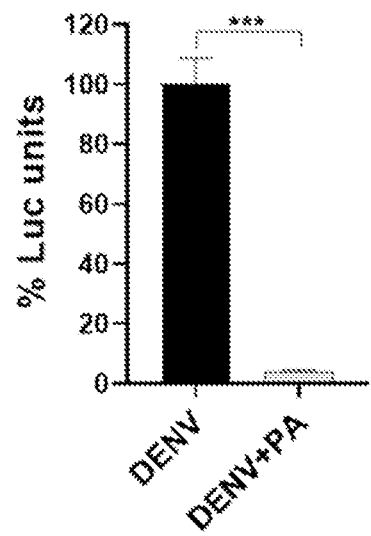
FIGS. 7G-7J show luciferase assay data for A549 cells pre-treated with 2 mM PA and infected with different luciferase reporter viruses for 48 hr.
Figure 7H:
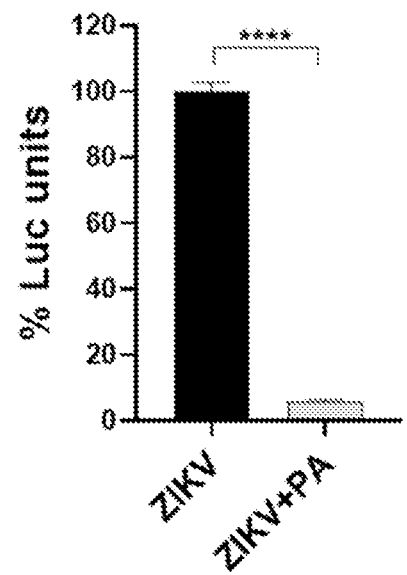
Figure 7I:
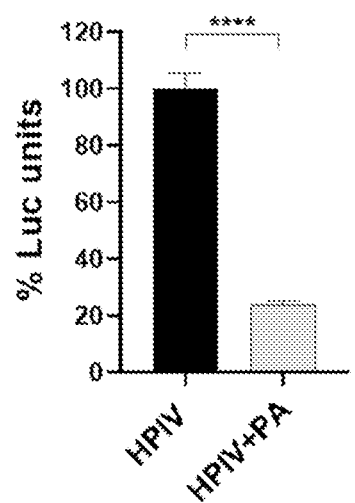
Figure 7J:
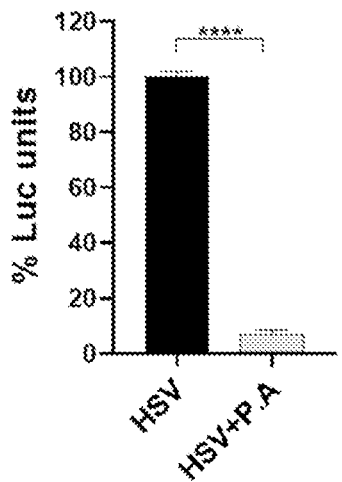
Figure 7K:
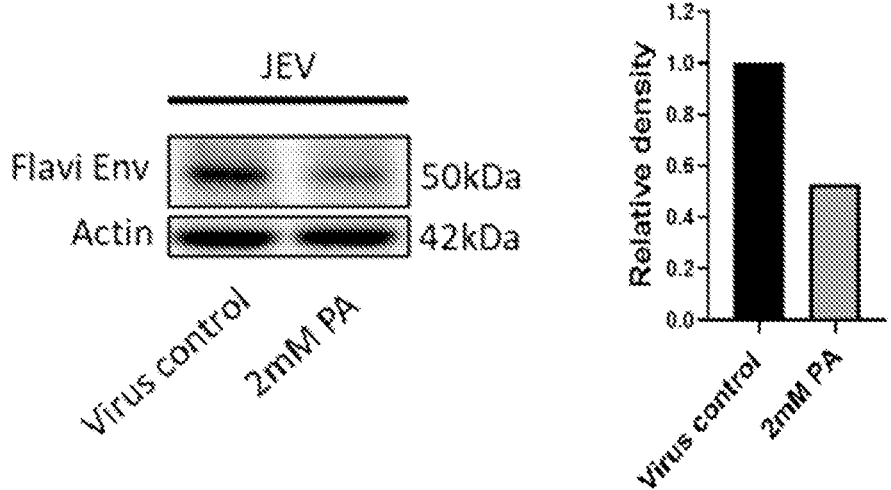
FIGS. 7K-7L show a western blot analysis of flavivirus envelope protein showing the inhibition of Japanese encephalitis Virus (JEV) clinical strain P20778, and wild type Zika virus (ZIKV) Cambodia strain.
Figure 7L:
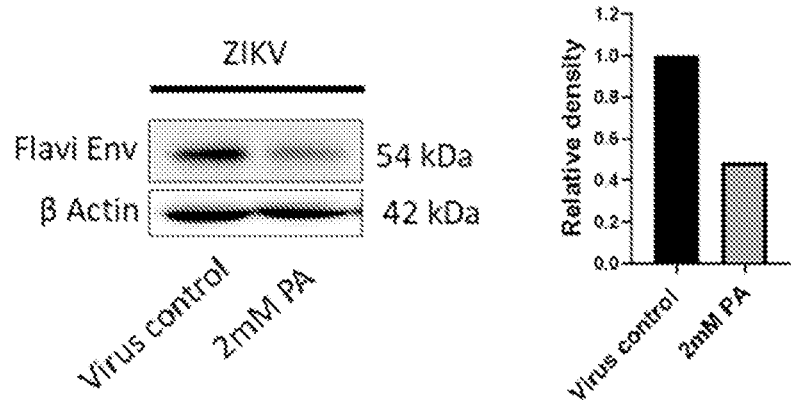
Figure 8A:
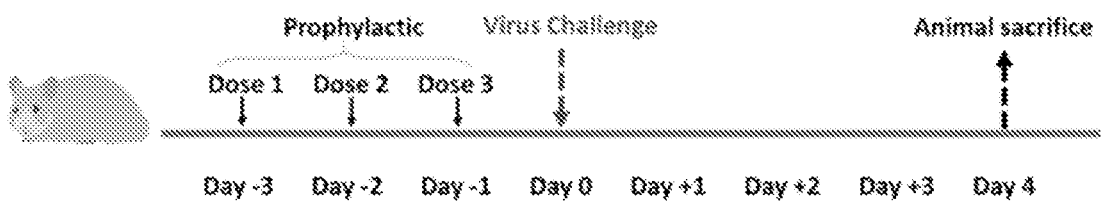
FIG. 8A shows a schematic for a prophylactic PA treatment regimen in hamsters.
Figure 8B:
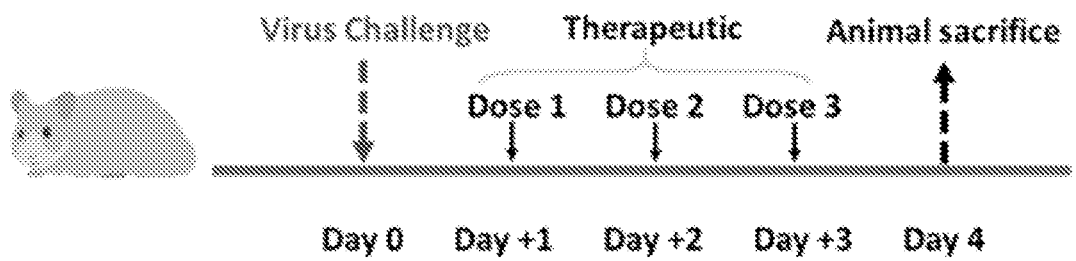
FIG. 8B shows a schematic for a therapeutic PA treatment regimen in hamsters. FIG.
Figure 8C:
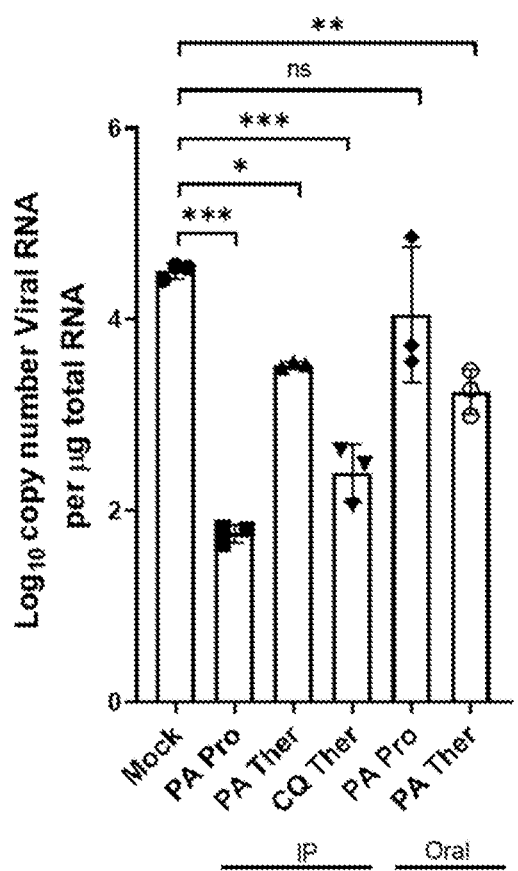
Figure 8D:
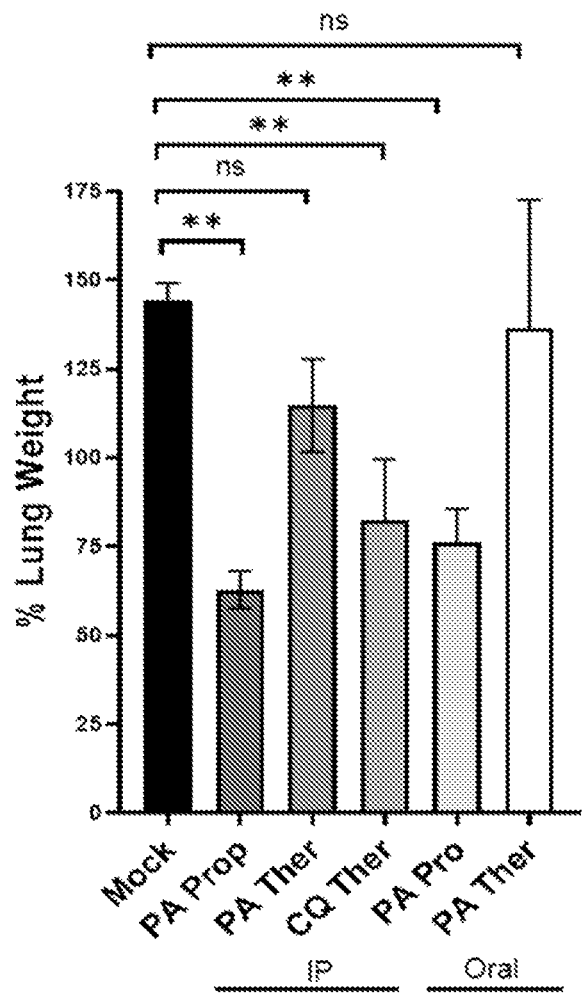
Figure 8E:
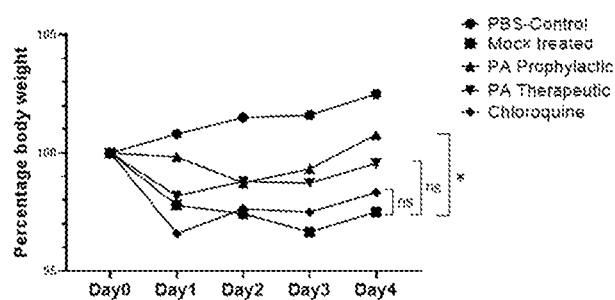
Figure 8F:
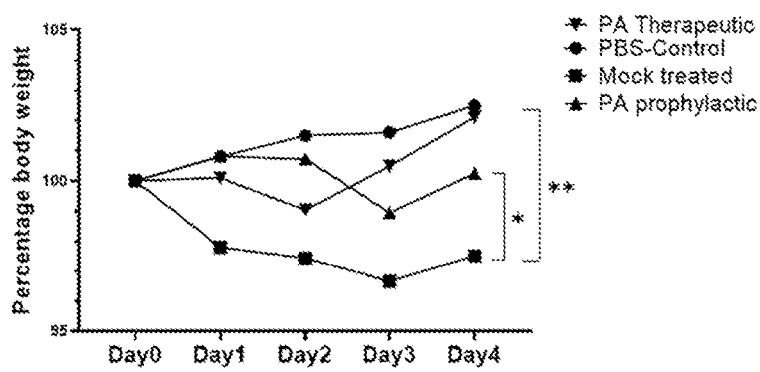
Figure 8G:
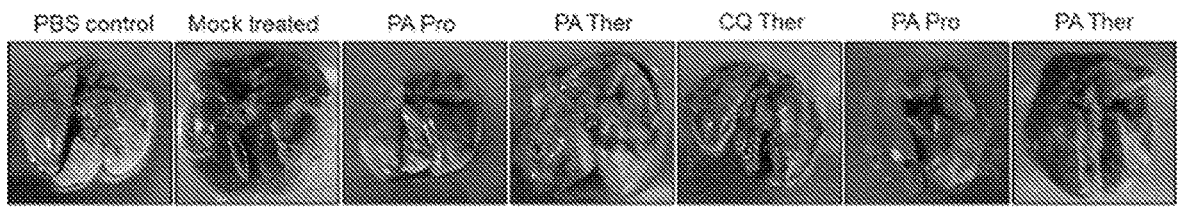
Figure 8H:
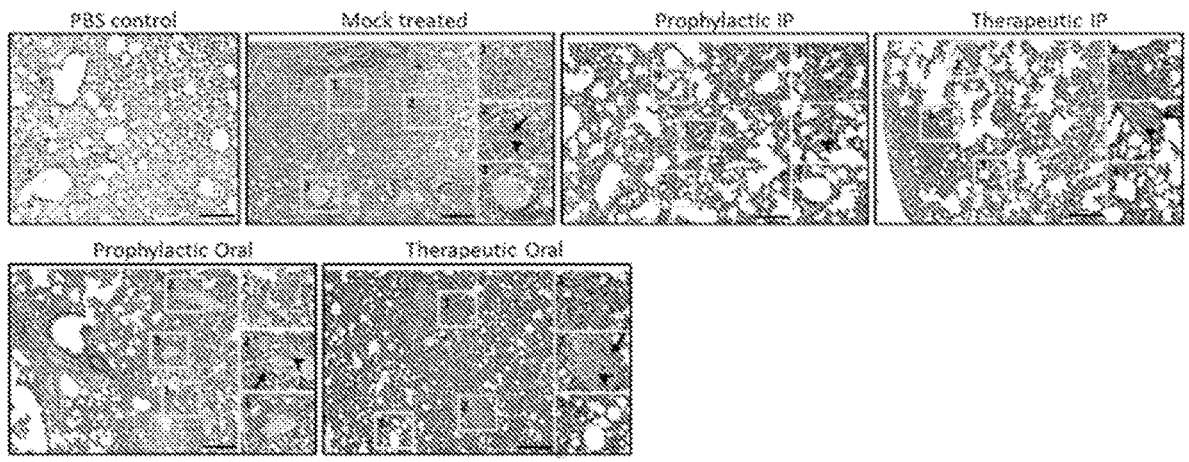
Figure 8I:
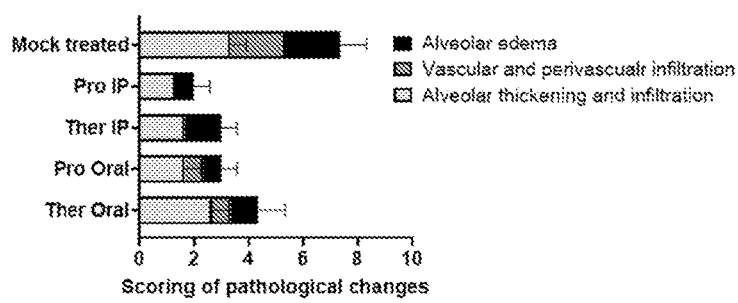
Figure 9A:
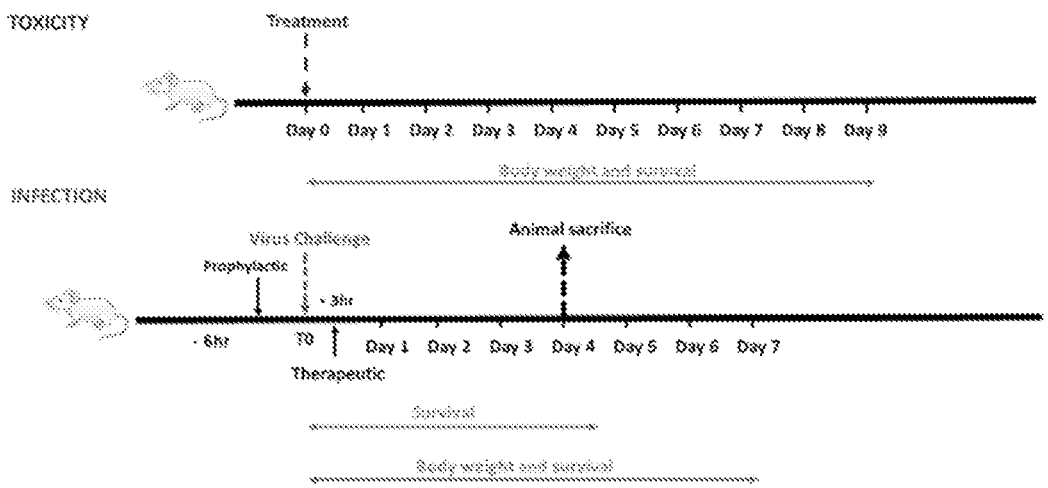
Figure 9B:
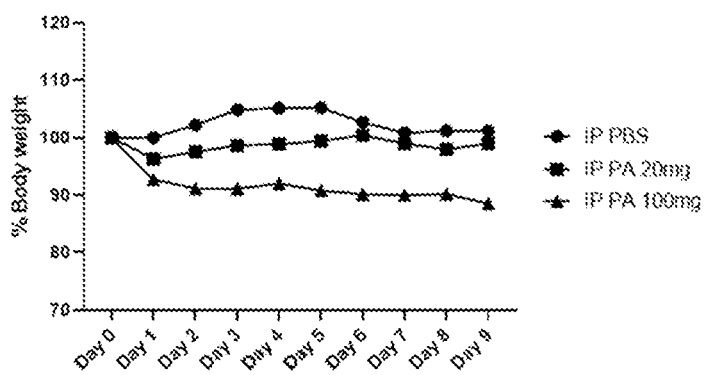
Figure 9C:
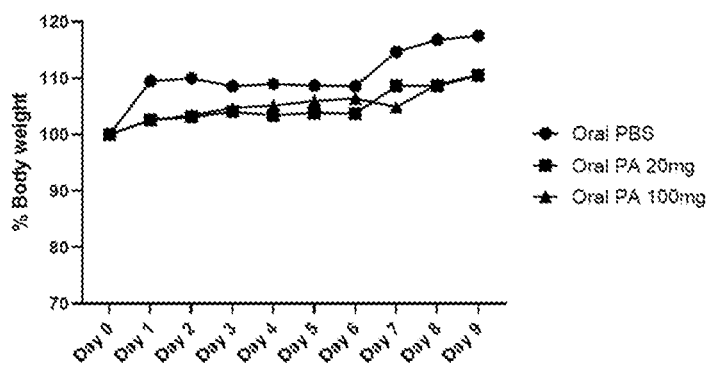
Figure 9D:
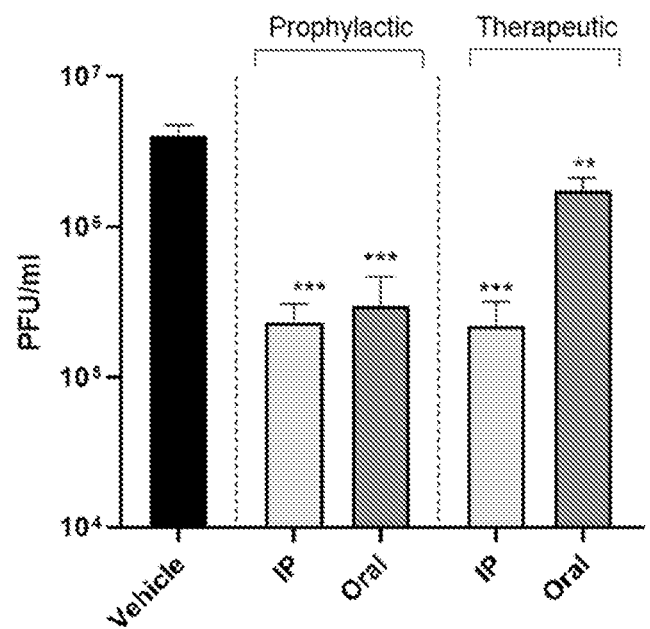
Figure 9E:
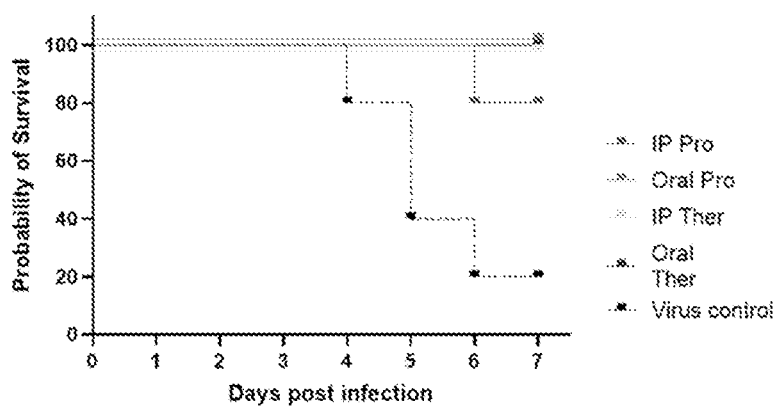
Figure 9F:
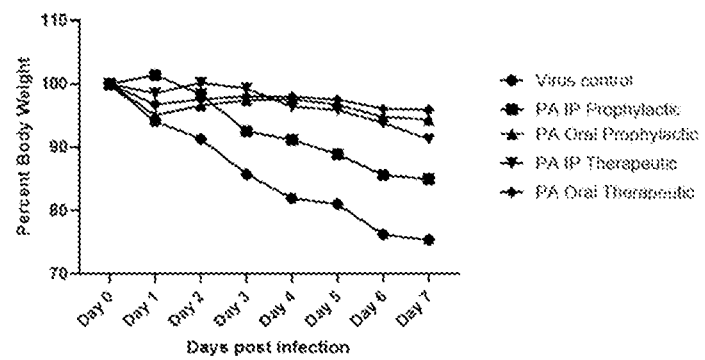
Figure 9G:
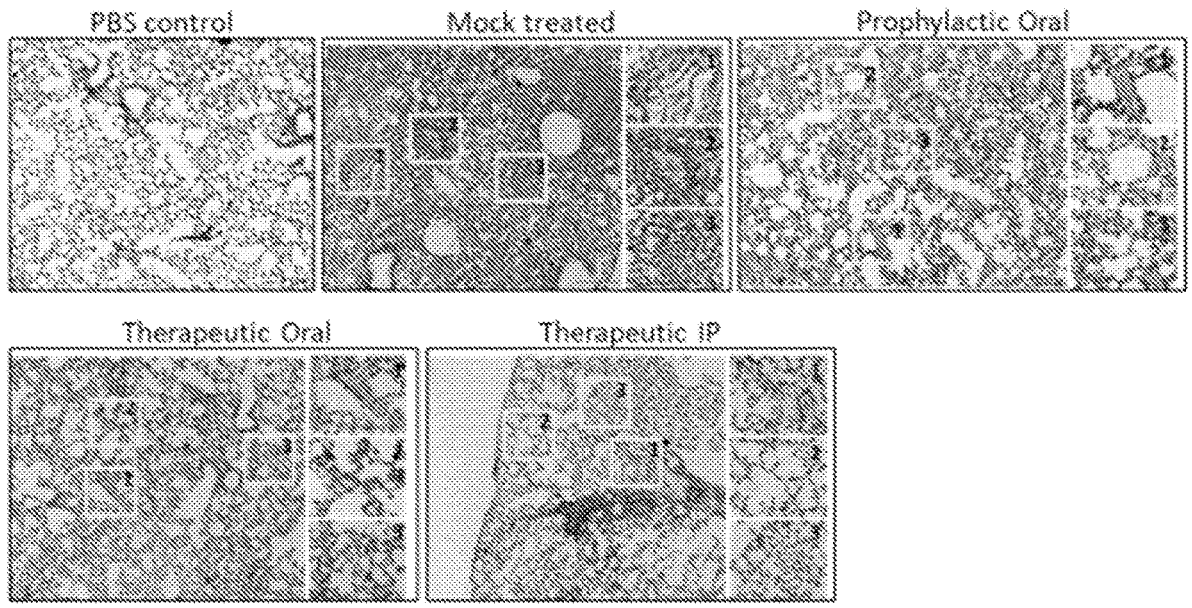
Figure 9H:
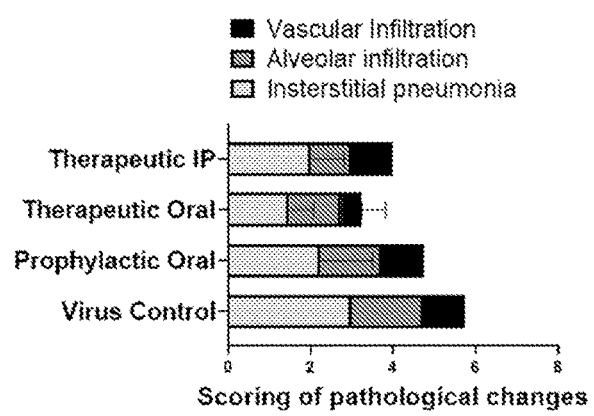
Figure 10A:
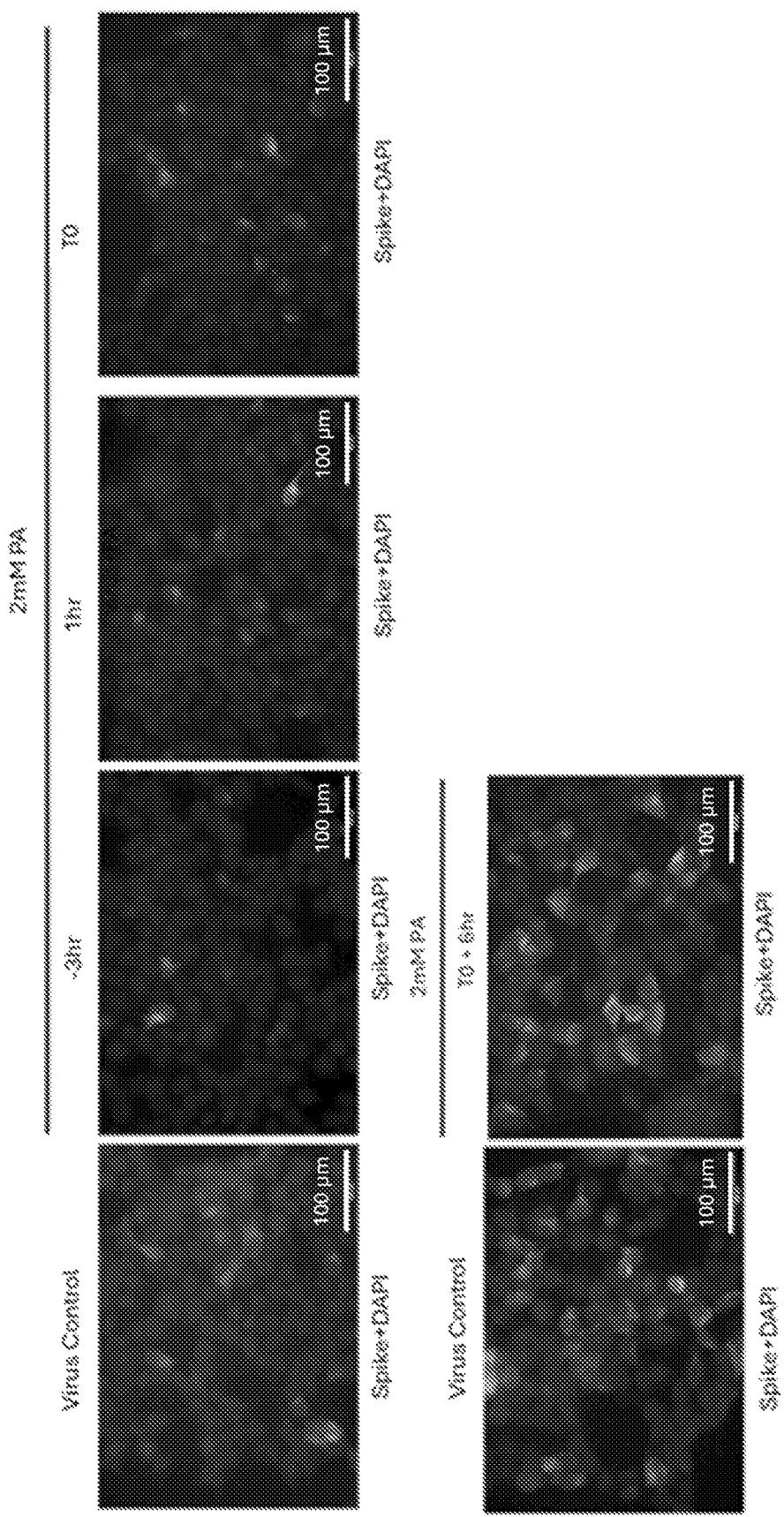
Figure 10B:
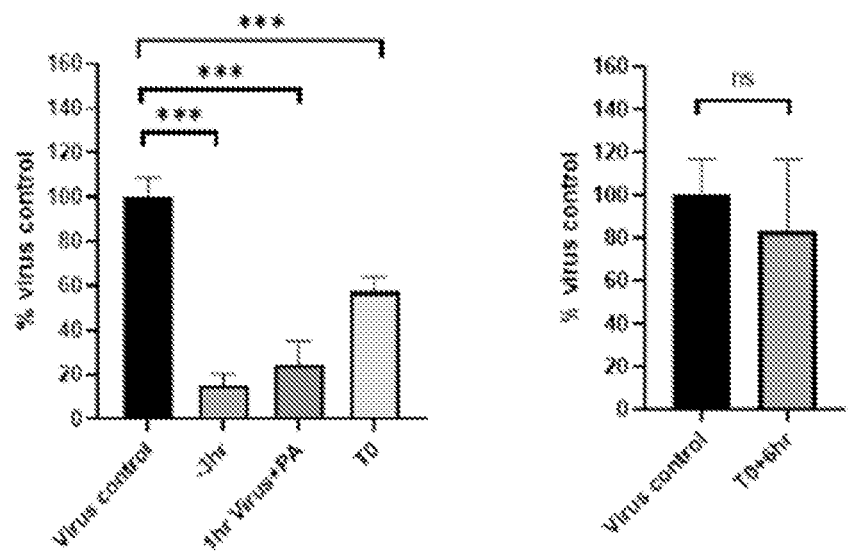
Figure 10C:
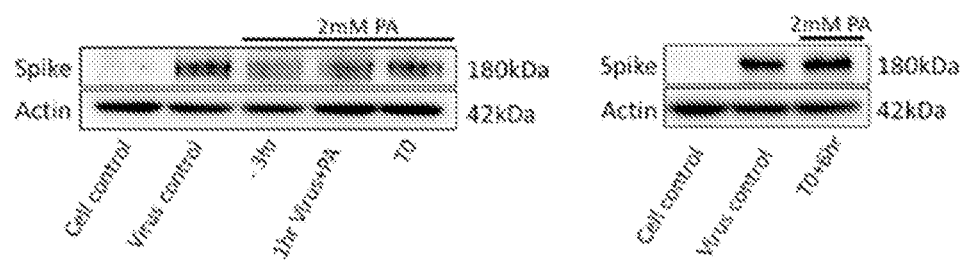
Figure 10D:
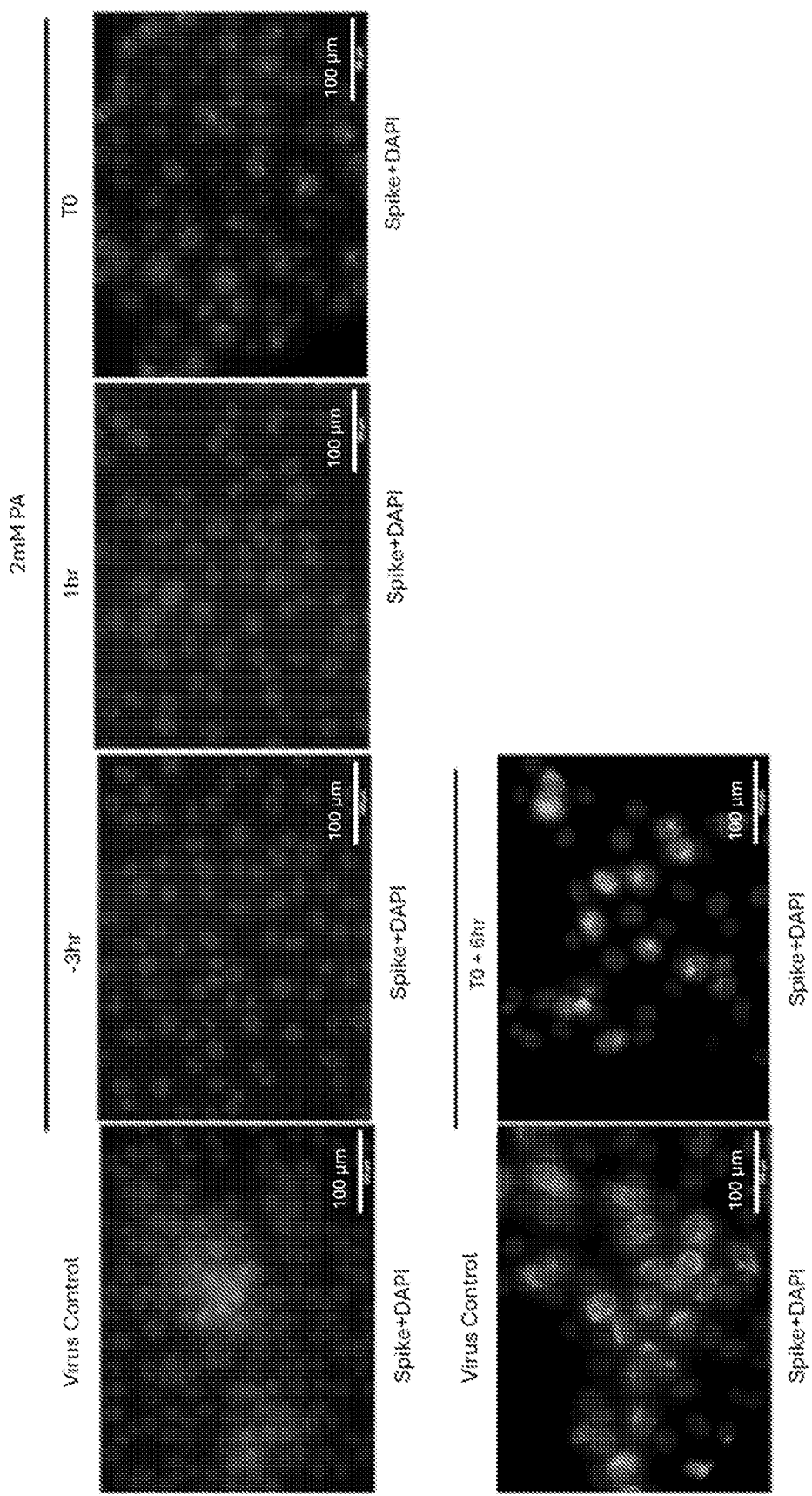
Figure 10E:
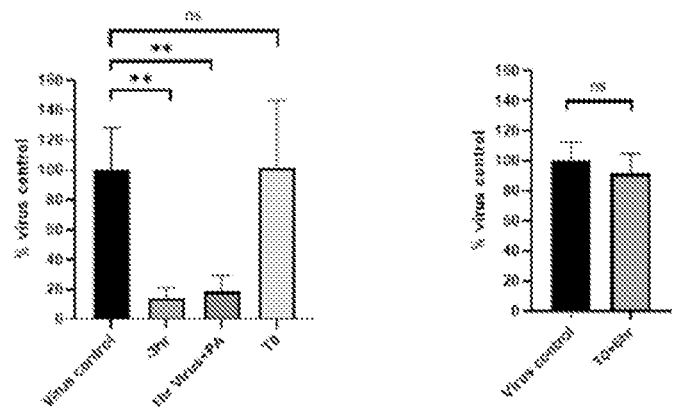
Figure 10F:
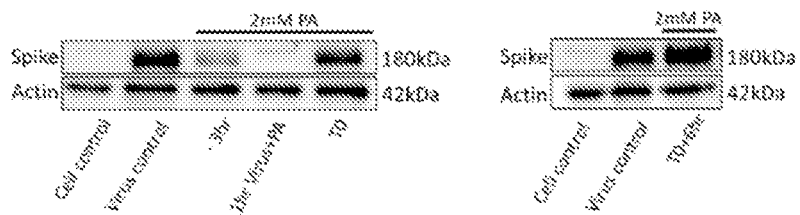
Figure 10G:
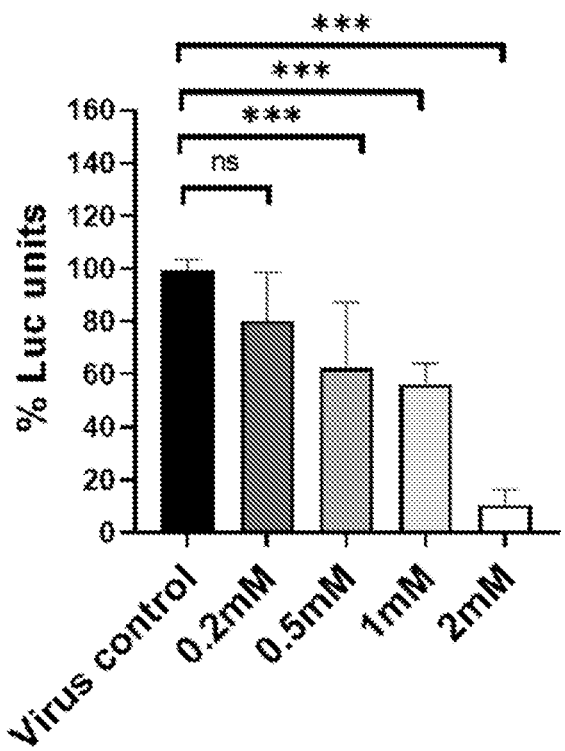
Figure 10H:
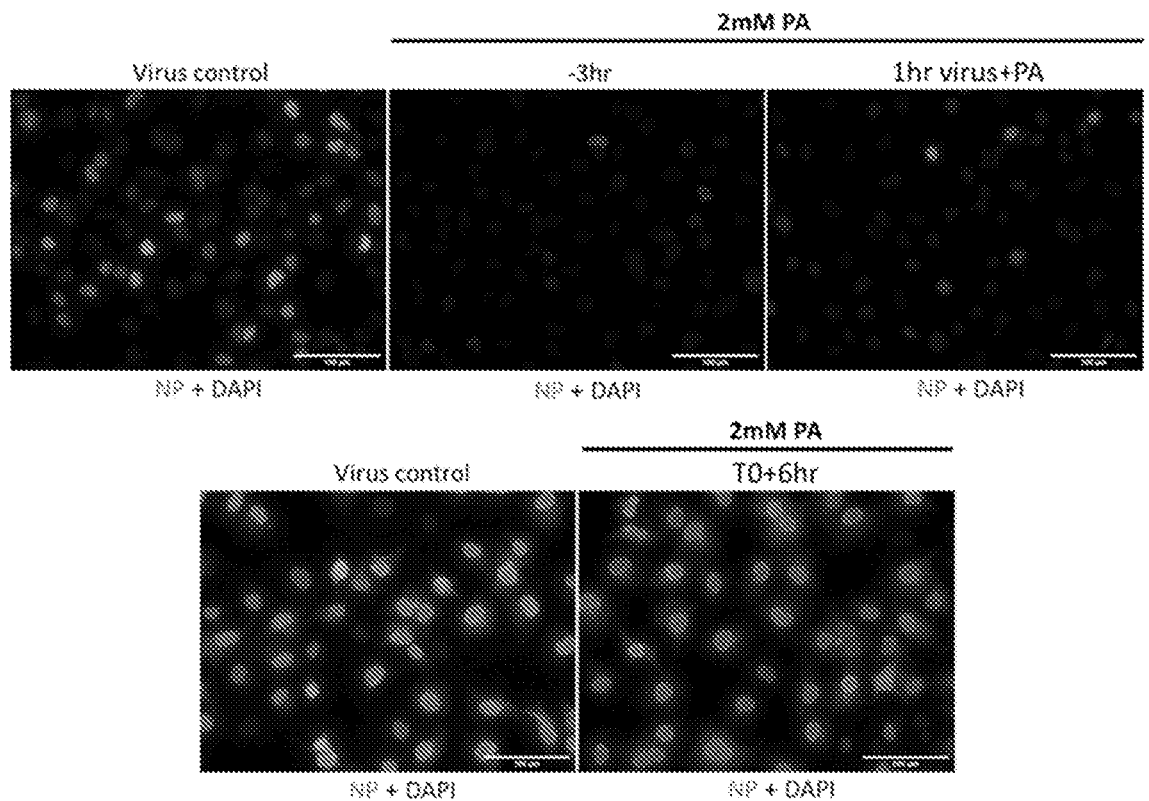
Figure 10I:
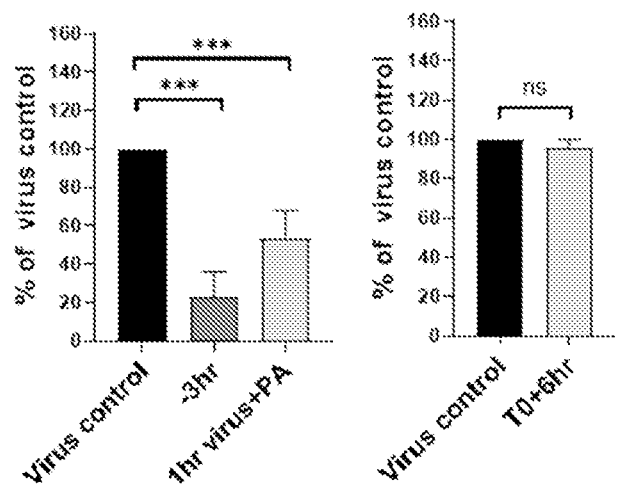
Figure 10J:
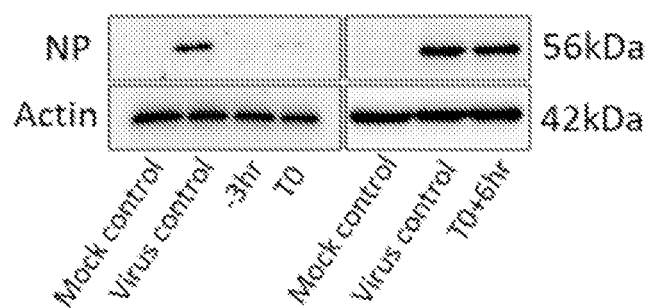
Figure 11A:
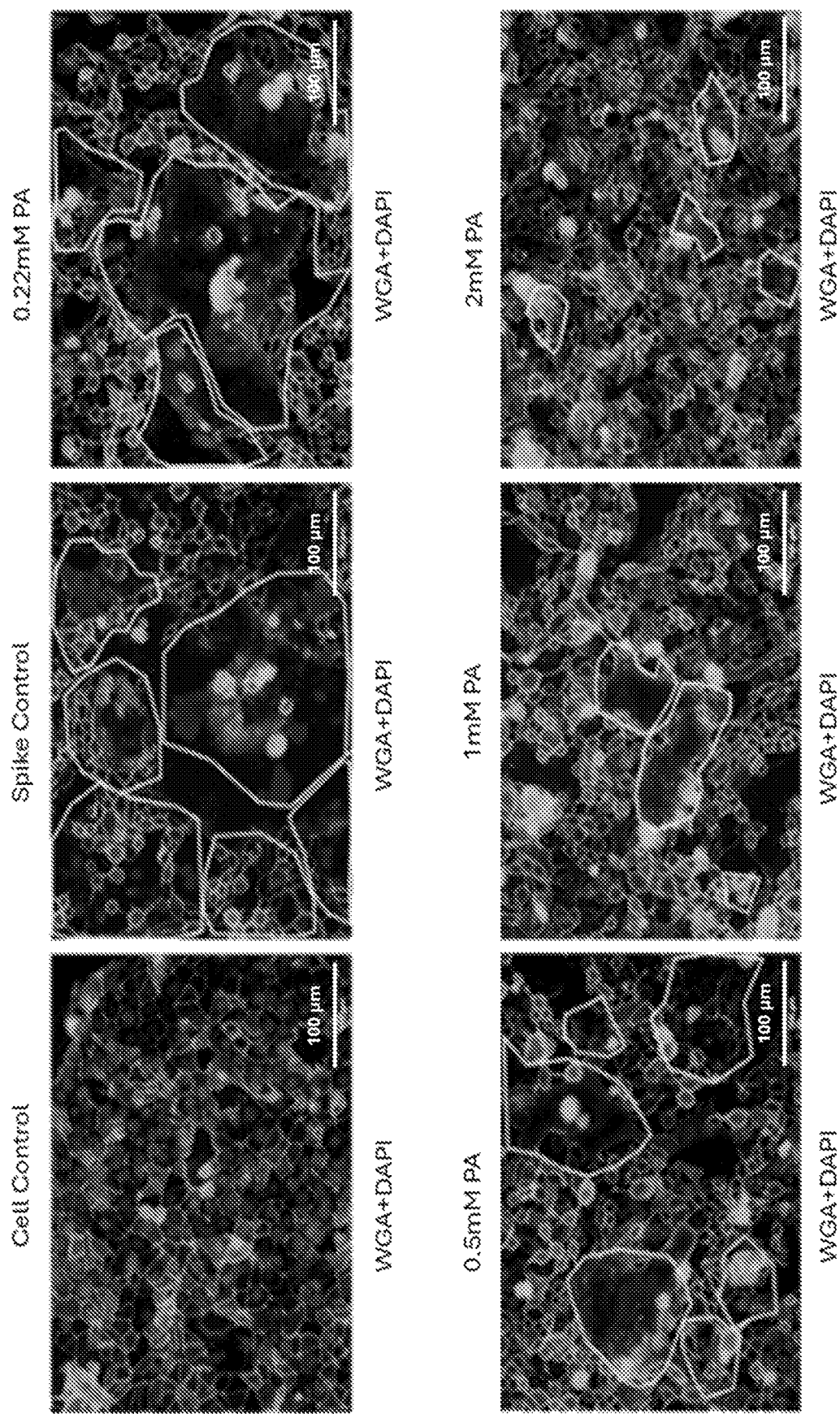
Figure 11A:
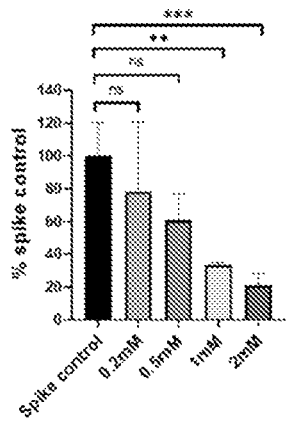
Figure 11B:
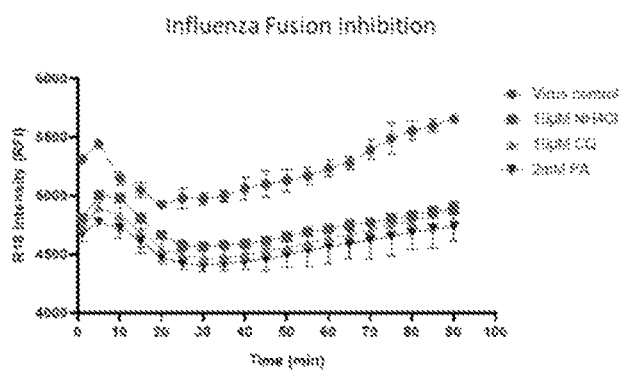
Figure 11C:
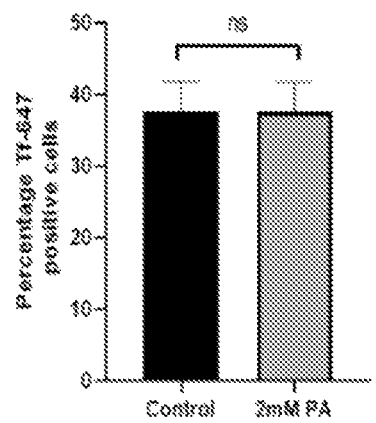
Figure 11D:
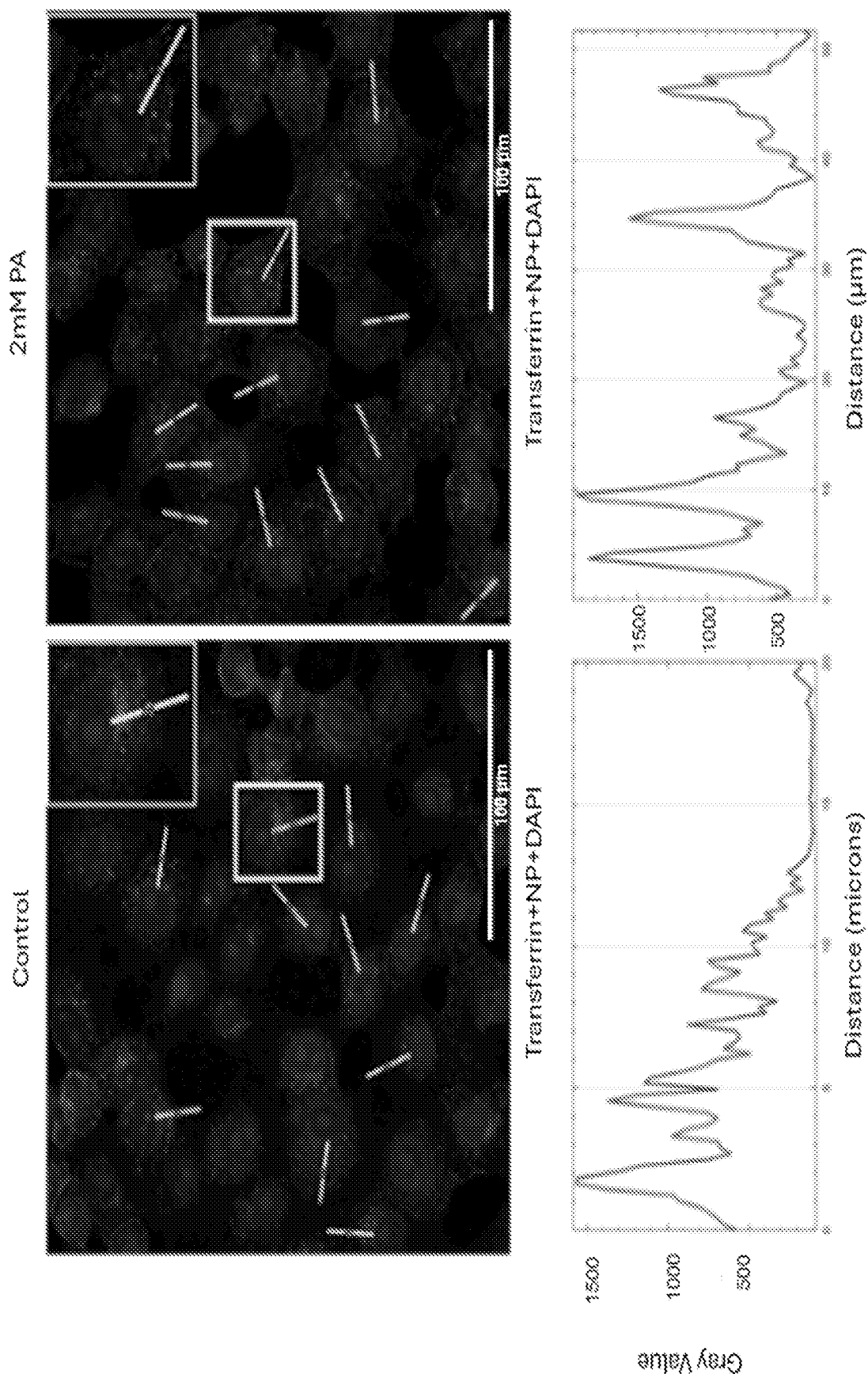
Figure 11E:
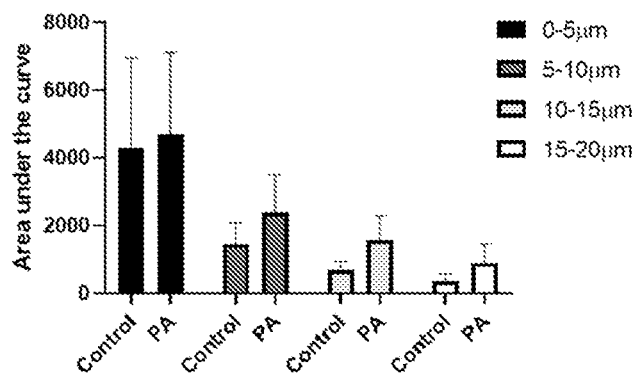
Figure 11F:
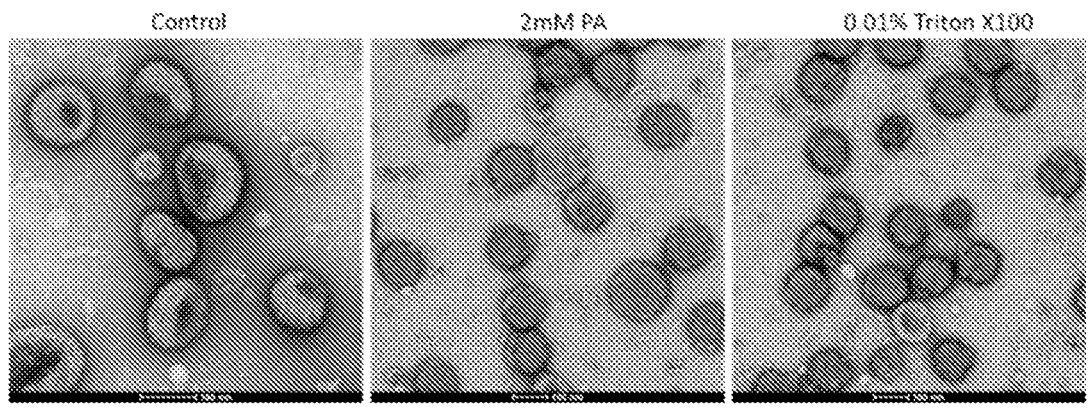
Figure 12A:
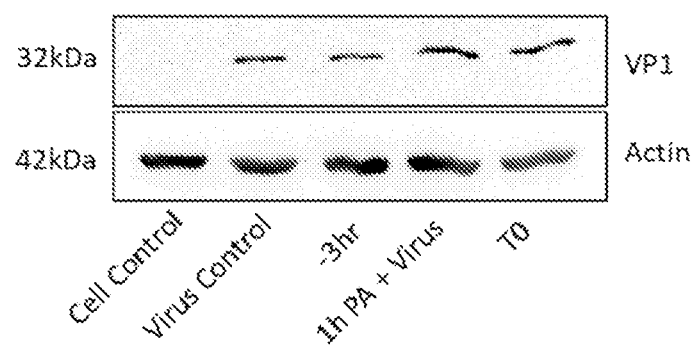
Figure 12B:
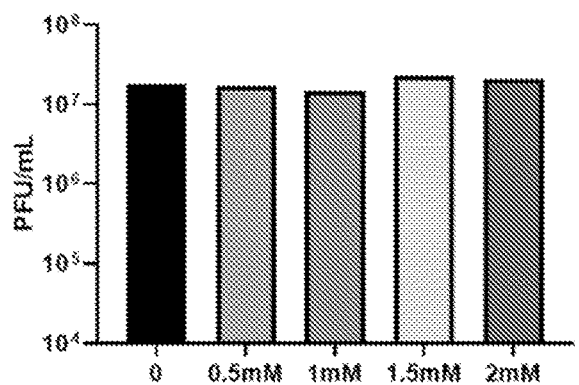
Figure 12C:
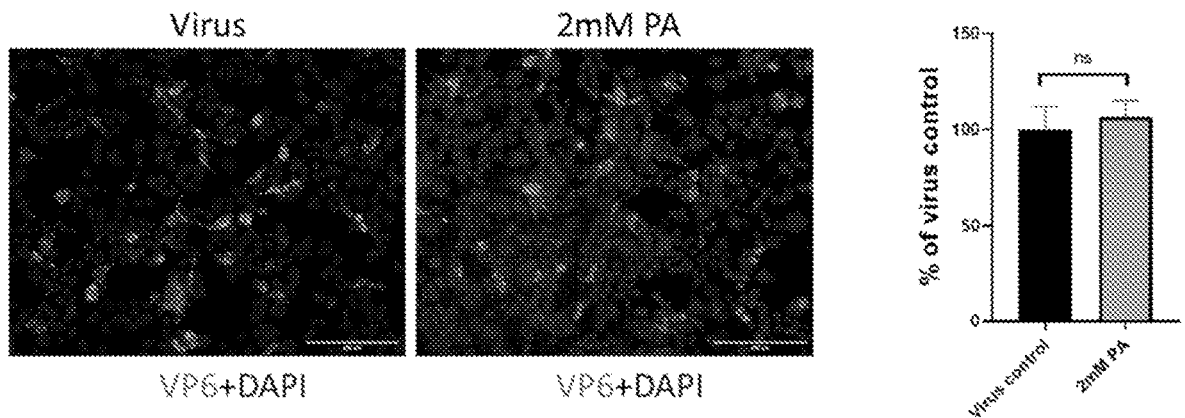
Figure 12D:
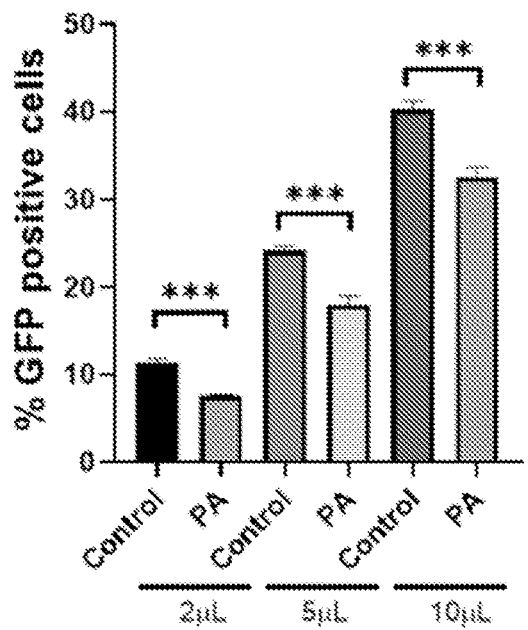
Figure 12E:
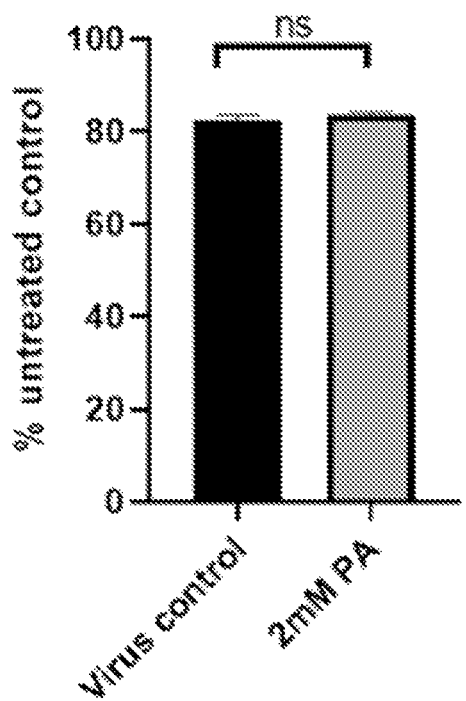
Figure 12F:
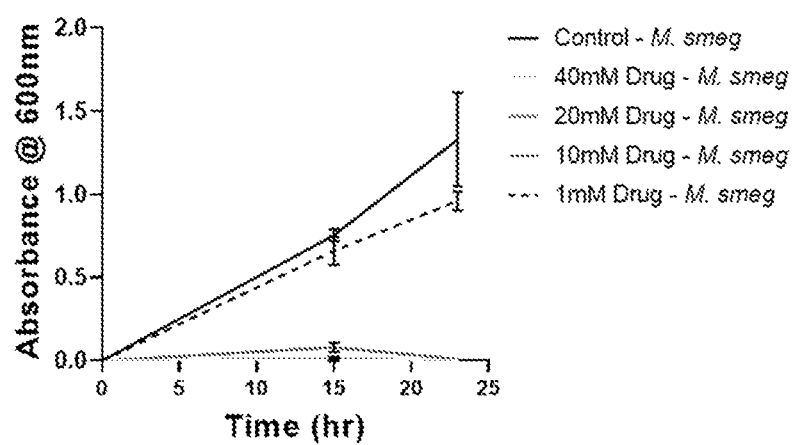
Figure 12G:
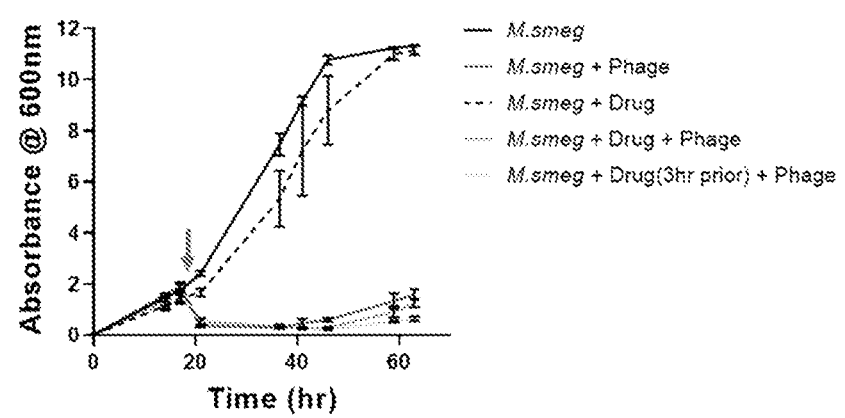

A three $log_{10}$ decrease in total viral RNA copy numbers was observed in both VeroE6 and HEK ACE2 cells treated with 2 mM PA, compared to almost 1 $log_{10}$ decrease seen in Calu3 cells. See FIG. 6.

These results indicate that PA exhibits potent antiviral activity against SARS-CoV-2 in cells lines of different species.

Example 7

Picolinic Acid Inhibits SARS-CoV-2 and a Range of Other Viruses

In this experiment, the in vitro antiviral efficacy of PA against SARS-CoV-2 was tested using cells lines from both human and non-human primate origin. To this end, HEK ACE2 cells were pre-treated for 3 hr with increasing doses of PA as indicated, infected with 0.1 MOI of either SARS-CoV-2 Hong Kong (FIG. 7, panel A) or four SARS-CoV-2 variants of concern (FIG. 7, panel B). Cells were collected 48 hr p.i, viral RNA copy estimated by qRT PCR and corresponding cell viability of uninfected drug treated cells were plotted. VeroE6 cells were infected with 0.001 MOI for all viruses as mentioned above (FIG. 7, panels C and 7D). Results showed a 4-log 5 reduction in viral RNA load upon treatment with non-toxic (2 mM) concentrations of PA (FIG. 7, panels A and C). In a similar experimental setup using Calu3 cells, 2 mM PA treatment resulted in a 2-log reduction in viral load (FIG. 7, panel E). Varying levels of inhibition were seen upon testing PA on SARS-CoV-2 variants of concern, best results being observed against alpha variant in HEK ACE2 cells, as evidenced by a 5-log reduction viral RNA load. A 2.5 log reduction in gamma variant, and ~1 log reduction was seen in the case of beta and delta variants (FIG. 7, panel B). Infection of VeroE6 cells resulted in comparatively higher viral loads in the untreated controls, which was in turn significantly abrogated by ~1 log for all 4 variants tested (FIG. 7, panel D).

To further investigate the broad-spectrum activity of PA, its effects against a panel of viruses including Influenza A viruses (IAVs) in MDCK cells were tested. MDCK cells pre-treated with increasing concentrations of PA were infected with 0.01 MOI of PR8 wild type virus and 48 hr p.i, virus from supernatants were quantified by plaque assay (FIG. 7, panel F). In the case of PR8 wild type virus, a dose dependent decrease in infectious virus was observed at 48 hr post infection (p.i), with maximum (50%) inhibition seen in the presence of 2 mM PA (FIG. 7, panel F). A549 cells pre-treated with 2 mM PA were infected with different luciferase reporter viruses as indicated. Cells were harvested 48 hr p.i for luciferase assay and data normalized with untreated control are shown (FIG. 7, panels G and J). A 3-fold reduction in X79 virus titer was seen at this concentration, compared to Cal/09 and HALo strains. Multi-cycle infection in A549 cells infected with DENV and Zika reporter viruses showed >90% inhibition in the presence of 2 mM PA (FIG. 7, panels G and H). The anti-flavivirus effects of PA was supported by inhibition of Japanese encephalitis Virus (JEV) clinical strain P20778, and wild type Zika virus (ZIKV) Cambodia strain as shown by western blot analysis of Flavivirus envelope protein (FIG. 7, panels K and L). Human parainfluenza virus (HPIV) and herpes simplex virus (HSV) reporter virus assays showed 80-90% inhibition at this drug concentration (FIG. 7, panels I and J).

Example 8

Picolinic Acid Inhibits SARS-CoV-2 in a Preclinical Animal Model

To understand whether PA shows antiviral effects against SARS-CoV-2 in vivo, in vivo studies were performed in Syrian golden hamsters. PA toxicity studies in BALB/c mice using 20 and 100 mg/kg body weight of drug revealed the latter to be toxic when administered via oral route (FIG. 9, panels B and C). Based on this, 20 mg/kg PA was used for all treatment regimens via both IP and oral routes in mice and hamsters. Prophylactic and therapeutic dosage regimens in hamsters are shown in FIG. 8, panels A and B respectively. Prophylactic treatment of hamsters involved administration of PA at 1, 2 and 3 days prior to infection, followed by virus challenge at day 0. Therapeutic treatment used dosage during 1, 2 and 3 dpi (days post-infection). Viral RNA copy number from lung tissue homogenates for both prophylactic and therapeutic treatment groups is shown in FIG. 8, panel C and corresponding total lung weight loss percentage up to 4 dpi is shown in FIG. 8, panel D. Administration of 20 mg/kg PA prophylactically by IP injection caused a ~2.5-fold reduction in lung viral load, compared to a 1 log decrease when the drug was delivered orally. Therapeutic treatment by both routes mitigated viral RNA load by ~1 log. These observations were consistent with both body weight as well as corresponding lung weight rescue, compared to mock treated animals (FIG. 8, panels D-F). FIG. 8, panel E shows a percentage bodyweight loss in the prophylactic group and FIG. 8, panel F shows a percentage bodyweight loss in the therapeutic treatment group. Upon dosage of CQ therapeutically, lung viral loads were reduced by ~1 log, compared to that of PA administered via the same route (FIG. 8, panel C). Images of whole lungs harvested from sacrificed animals manifested gross pathology and inflammation in mock treated, compared to the healthy control, with much of the pathology reduced in lungs from PA treated groups (FIG. 8, panel G). FIG. 8, panel H shows histology images of lung tissue sections for all treatment groups including mock infected and healthy controls. Scoring of histology sections was done based on following criteria (1) alveolar edema, (2) vascular and perivascular infiltration (3) alveolar thickening and infiltration. Scoring was done based on severity on a scale of 1-4 (1-mild, 2-moderate, 3-severe, 4-very severe). An overall score was given by accumulating the total scores for each criterion, results are shown in (I). Evidence from histopathology analysis and scoring clearly showed decreased pathology (FIG. 8, panels G and H).

Example 9

Picolinic Acid Inhibits Influenza A Virus in Mice Model

In view of the broad-spectrum activity of PA across multiple cell lines, and efficacy versus SARS CoV-2 inferred from the above studies in hamsters, the effect of PA in mitigating other viruses was studied in vivo in a mouse model. FIG. 9, panel A shows schematics showing toxicity and infection/treatment schedule for Influenza A virus (IAV) infection in BALB/c mice. Toxicity studies in BALB/c mice used administration of PA via oral or IP routes and monitoring of bodyweight up to day 9 post treatment. Toxicity results with bodyweight changes over 9 days post treatment with 20 mg/kg PA and 100 mg/kg PA delivered via IP and oral routes are shown in FIG. 9, panels B and C respectively. Based on these studies, 20 mg/kg PA dose was selected.

Prophylactic and therapeutic treatment used administration of PA 6 hr prior and 3 hr post infection respectively, survival was monitored up to day 4 p.i and bodyweight loss for remaining animals till day 7. FIG. 9, panel D shows a plaque assay quantification of infectious virus titer from lungs tissue homogenates. The plaque assay quantification showed >10-fold reduction in mice treated prophylactically with 20 mg/kg PA via oral and IP routes. Therapeutic treatment was more effective in abrogating lung virus titers when the drug was administered via IP route (FIG. 9, panel D). FIG. 9, panels E and F show a percentage survival and body weight loss up to day 7 post infection, respectively. The treatment of mice with PA was shown to completely rescue animal survival in all the groups tested, except for IP prophylactic (80% survival), over the course of 7 days p.i (FIG. 9, panel E). Over 90% rescue of total animal body weight was seen for all groups. Mice bodyweight from IP prophylactic group declined from day 2, but still showed >10% rescue compared to virus control at day 7 (FIG. 9, panel F). FIG. 9, panel G shows histology images of mice lung specimens for all treatment groups including mock infected and healthy controls. Histology analysis showed marked reduction in pathology, with best rescue observed in therapeutic oral group. Histology sections were scored based on the following clinical criteria, namely (1) vascular infiltration, (2) alveolar infiltration and (3) interstitial pneumonia. Scoring was done based on severity on a scale of 1-4 (1-mild, 2-moderate, 3-severe, 4-very severe). An overall score was given by accumulating the total scores for each criterion, the results are shown in FIG. 9, panel H. All treated groups showed recovery, as evidenced by the clinical scores shown in FIG. 9, panel H.

Example 10

Time of Addition Studies Reveal Inhibition of Virus Entry as Mechanism of Action for Picolinic Acid Antiviral Activity To identify the mechanism of action (MoA) of PA on viruses, time of addition assays were employed wherein cells were treated with PA at different time points before and after infection. Specifically, cells were either pre-treated for 3 hr with 2 mM PA, infected with 10 MOI SARS-CoV-2 in presence of PA and collected 3 hr later (−3 hr); or treated during infection (T0); or PA was added 6 hr p.i and collected a further 3 hr later (T0+6 hr); or virus and PA were incubated together for 1 hr and used for infection (1 hr virus+PA). SARS-CoV-2 infection of pre-treated HEK ACE2 (FIG. 10, panels A-C) and VeroE6 (FIG. 10, panels D-F) cells with 2 mM PA for 3 hr mitigated virus replication by >80% as shown by IFA images and quantification of cells positive for virus spike protein associated immunofluorescence (FIG. 10, panel A and panel B, left graph). Similar effects were also seen when virus and drug were incubated for 1 hr before infection. However, when cells without pre-treatment with PA were infected in the presence of drug (T0), almost no inhibition was observed in either cell line (FIG. 10, panel A, panel B-left graph, panel D, and panel E-left graph). These findings were supported by western blot data for virus spike protein (FIG. 10, panels C and F). To test effects of PA on post-entry stages of virus replication cycle, drug was added 6 hr post infection and collected 3 hr later. Here, ~50% inhibition of virus was observed in HEK ACE2 cells and no inhibition was found in VeroE6 cells, as seen by IFA images (FIG. 10, panel A, panel B-right graph, panel D, and panel E-right graph) and western blot analysis (FIG. 10, panels C and F-right graphs).

HEK ACE2 cells pre-treated with 2 mM PA were infected with SARS-CoV-2 spike pseudotyped particles in the presence of PA and harvested 60 hr later. Results show firefly luciferase values normalized to virus control. Infection of HEK ACE2 cells using SARS-CoV-2 spike pseudotyped particles in the presence of increasing PA concentrations revealed a dose-dependent effect, with 90% inhibition at 2 mM concentration (FIG. 10, panel G).

Entry effects of PA against PR8 WT virus were tested in A549 cells. Specifically, A549 cells were either pre-treated for 3 hr with 2 mM PA, infected with 2 MOI PR8 WT in presence of drug and collected 3 hr later (−3 hr); virus was incubated with 2 mM PA for 1 hr and used for infection (1 hr virus+PA); or PA was added 6 hr p.i and collected a further 3 hr later (T0+6 hr). IFA results showed 80% inhibition upon 3 hr pre and post treatment with PA (FIG. 10, panels H and I). As in the case of SARS-CoV-2, when virus was incubated with drug, and subsequently used for infection, a 50% inhibition was seen, as observed by IFA for virus nucleoprotein and western blot (FIG. 10, panels H and I). No differences were observed when PA was added 6 hr post infection (FIG. 10, panels H and I). The findings from IFA were also reflected in western blot analysis of the same samples (FIG. 10, panel J).

Example 11

Picolinic Acid Inhibits Virus-Membrane Fusion, Disrupts Viral Envelope

To understand the precise mechanism of action mediating inhibition of virus entry, the effects of PA on virus spike mediated syncytia formation were studied using SARS-CoV-2. VeroE6 cells transfected with a plasmid expressing SARS-CoV-2 spike protein were treated with increasing concentrations of PA, and 24 hr later, fixed and labelled with wheat germ hemagglutinin (WGA) and DAPI. Area of syncytia was quantified using ImageJ/Fiji and plotted as percentage of untreated control (FIG. 11, panel A). Results showed a dose-dependent inhibition of virus spike induced syncytia formation. 1 and 2 mM PA treatment resulted in 70 and 80% inhibition of syncytia respectively, as shown by IFA images and quantification of syncytia from respective treatment conditions (FIG. 11, panel A).

Next, the effects of PA in inhibiting influenza virus-endosome fusion were tested. A549 cells were pre-treated with either 2 mM PA, 10 µM NH4Cl or 10 µM CQ, infected with R18 labelled PR8 WT virus on ice, transferred to a plate reader at 37° C. and the increasing fluorescence signal associated with virus-endosome fusion during virus entry was quantified over a period of 90 min at 10 min intervals. Results shown in FIG. 11, panel B show that cells treated with 2 mM PA or control drugs 10 µM ammonium chloride (NH4Cl) and 10 µM Chloroquine diphosphate (CQ) were all able to inhibit virus-entry associated increase in fluorescence intensity.

Next, fluorescent transferrin conjugates (Tf 647) were used to test the possible effects of PA on clathrin mediated endocytosis. A549 cells pre-treated with 2 mM PA were pulsed with 25 µg/mL Tf647 for 1 hr in the presence of PA, washed and analyzed by flow cytometry to quantify the percentage of Tf647 positive cells. 1 hr pulse of A549 cells with Tf647 in the presence of 2 mM PA did not show any differences in cellular uptake of transferrin (FIG. 11, panel C). Further, the intracellular localization of Tf647 labelled endocytic vesicles in PR8 WT virus infected VeroE6 cells treated with 2 mM PA was studied. PA treated VeroE6 cells were incubated with Tf647 and 100 MOI PR8 WT virus for 1 hr on ice and moved to 37° C. After 1 hr, cells were washed and incubated for 15 min at 37° C. before fixation with 4% formalin. Images were acquired using a confocal microscope and distance of Tf647 labelled vesicles from nuclei was quantified using Imagej/Fiji. A characteristic scattering of Tf647 loaded endocytic vesicles and influenza virus NP labelled PR8 WT virus particles in drug treated cells was observed (FIG. 11, panel D). Quantification of Tf647 associated fluorescence intensity showed endocytic vesicles in PA treated cells to be localized up to 15-20 microns away from the nuclei (FIG. 11, panel E).

Furthermore, Transmission electron microscopy (TEM) imaging of PA treated PR8 WT virus particles was employed to study whether the virus entry targeting effects of PA is due to disruption of virion structural integrity. For this, PR8 WT virus particles were incubated with either 2 mM PA, 0.01% Triton X100 or distilled water for 3 hr, mounted on copper grids and stained with uranyl acetate for TEM imaging. Results showed severe disruption of viral envelope compared to untreated control. The positive control using 0.01% Triton X 100 treated virus particles also showed similar effects on these viruses (FIG. 11, panel F).

Example 12

Picolinic Acid Exhibits Limited Antiviral Activity Against Naked Viruses, Does Not Affect Bacteriophages The effects of PA against non-enveloped viruses were tested to see if PA would be effective against non-enveloped viruses as well. To this end, HeLa cells were either pre-treated for 3 hr with 2 mM PA, infected with 10 MOI Coxsackie virus B3 in presence of PA and collected 3 hr later (−3 hr); or treated during infection (T0); or virus and PA were incubated together for 1 hr and used for infection (1 hr virus+PA). FIG. 12, panel A shows quantification of virus infection by western blot using VP1 antibody. The data showed that pre-treatment of cells, incubation of virus with drug prior to infection, and treatment at the time of infection, did not have any effects on virus entry, as seen by western blot data for virus VP1 protein (FIG. 12, panel A).

Further, Vero cells were pre-treated with increasing concentrations of PA as indicated and infected with 0.1 MOI CVB3 in the presence of drugs. 48 hr p.i, cell culture supernatants were used to quantify infectious virus by plaque assay. Infectious virus from cell culture supernatants was quantified by plaque assay and results did not imply any differences across the multiple PA doses tested (FIG. 12, panel B).

Next, HEK cells pre-treated with 2 mM PA were infected with Rota virus RRV strain, fixed with 4% formalin after 12 hr and immunolabelled with VP6 antibody and DAPI to label the virus particles and nuclei respectively. Percentage positive cells was quantified using ImageJ/Fiji. The data showed that pre-treatment of cells did not have any effects on virus entry as shown by IFA images and quantification of VP6 positive cells (FIG. 12, panel C).

HEK cells pre-treated with 2 mM PA were infected with AAV6-GFP particles in presence of drug at different volumes as indicated. 48 hr p.i, cells were harvested and analyzed for GFP positive cells by flow cytometry. HEK cells infected with increasing volumes of the AAV6-eGFP preparations in the presence of 2 mM PA, resulted in 5-10% decrease in GFP positive cells in all conditions tested (FIG. 12, panel D). In a similar experimental setup, HEK cells pre-treated with 2 mM PA were infected with 10 MOI Adenovirus 5 expressing eGFP in the presence of drug and harvested 24 hr later for quantification of GFP positive cells by flow cytometry. Almost no differences were observed between GFP positive HEK cells in treated and untreated conditions (FIG. 12, panel E).

Since most of the naked viruses tested were not inhibited by PA, whether PA would be effective against TM4 mycobacteriophages. *M. smegmatis* cells in a 48 well plate were treated with increasing concentrations of PA as indicated and OD600 measurements were taken periodically up to 24 hr. The data showed the least concentration of 1 mM PA to be non-toxic (FIG. 12, panel F). For the antiviral assay, 1 mM PA was either added at the start of experiment or 3 hr prior to infection. In either case, there was no protection from TM4 mycobacteriophage induced cell death (FIG. 12, panel G).

Example 13

Methods Detail for Examples 7-12

Ethics Statement

The study designs were reviewed and approved by institutional biosafety committee guidelines, (IBSC/IISc/ST/17/2020), following the Indian Council of Medical Research and Department of Biotechnology recommendations. All experiments involving animals were reviewed and approved by the Institutional Animal Ethics Committee (Ref: IAEC/IISc/ST/784/2020) at the Indian Institute of Science and conducted in a Viral Biosafety level-3 facility. The experiments were performed according to CPCSEA (The Committee for the Purpose of Control and Supervision of Experiments on Animals) guidelines.

Cells and Plasmids

The following cell lines were used in this study: HEK 293T cells expressing human ACE2 (NR-52511, BEI Resources, NIAID, NIH); HEK 293T, VeroE6 (CRL-1586, ATCC®); Madin-Darby Canine Kidney (MDCK); A549 Human Lung Carcinoma (NR-52268, BEI Resources, NIAID, NIH), Calu-3 (ATCC HTB-55) and BHK-21. All cell lines were cultured in complete Dulbecco's modified Eagle medium (12100-038, Gibco) with 10% HI-FBS (16140-071, Gibco), 100 IU/ml Penicillin and 100 µg/ml Streptomycin (15140122, Gibco) supplemented with Gluta-MAX™ (35050-061, Gibco).

Viruses

The following SARS-CoV2 isolates were procured from BEI Resources, NIAID, NIH: Isolate Hong Kong/VM20001061/2020, NR-52282; Isolate hCoV-19/England/204820464/2020 (Lineage B.1.1.7—Alpha variant), NR-54000; Isolate hCoV-19/USA/MD-HP01542/2021 (Lineage B.1.351 South Africa—Beta variant), NR-55282; Isolate hCoV-19/USA/PHC658/2021 (Lineage B.1.617.2; Delta Variant), NR-55611; Isolate hCoV-19/Japan/TY7-503/2021 (Brazil P.1 Gamma variant), NR-54982. All these viruses were propagated and titrated by plaque assay in Vero E6 cells as described before (Case et al., 2020). The following Influenza A virus (IAV) strains namely A/Puerto Rico/8/1934 (PR8), A/California/04/2009 H1N1 (Cal/09), Viet Nam/1203/04 H5N1 (HALo), and A/reassortant/X-79 (Philippines/2/1982 x Puerto Rico/8/1934) (X79) were propagated in 11-day old embryonated chicken eggs and titrated by plaque assay in MDCK cells (Gaush and Smith, 1968).

Japanese Encephalitis Virus (JEV) clinical strain P20778 was propagated and titrated in BHK-21 cells. The reporter viruses used in this study include IAV expressing Gaussia luciferase (NS1 Luc) (Eckert et al., 2014); Dengue virus (DENV Luc), Zika Luc, Human parainfluenza virus (HPIV Luc) and Herpes Simplex Virus (HSV Luc) expressing renilla luciferase.

Adenovirus Serotype 5, Clone Ad5-CMV-hACE2/RSV-eGFP, Recombinant Expressing Human ACE2 was procured from BEI resources (Catalog No. NR-52390).

Coxsackie virus B3 was a kind gift from Prof. Saumitra Das, Department of Microbiology and Cell Biology, Indian Institute of Science, Karnataka.

Rota virus RRV strain was a kind gift from Prof. Durga Rao.C, SRM University, Andhra Pradesh.

TM4 mycobacteriophage (Bajpai et al., 2018) was amplified in *M. smegmatis* and phage enumeration was done using the soft agar overlay technique as reported by Kalapala et al (Kalapala et al., 2020).

SARS CoV-2 Multi-Cycle Experiments

HEK ACE2 or Vero E6 cells were seeded in 24-well cell culture plates to reach 70-80% confluency next day. Cells were pre-treated with 0.25, 0.5, 1 and 2 mM PA for 3 hr and infected with 0.1 MOI or 0.001 MOI SARS-CoV-2 Hong Kong strain in HEK ACE2 and Vero E6 cells respectively in the presence of drug. For infection, cells were first incubated with 100 µL per well of inoculum and after 1 hr adsorption, topped up with 400 µL medium. DMEM containing 2% FBS was used for infection in Vero E6 cells and complete DMEM was used for HEK ACE2 cells. After 48 hr, total RNA from infected cells was extracted using Trizol and viral copy number was estimated by qRT PCR. Cell viability of uninfected, drug treated cells was measured using Alamar blue cytotoxicity assay (DAL 1025, Invitrogen) as per manufacturer's instructions.

Similarly, the effect of PA against SARS-CoV-2 variants of concern was tested by first pre-treating HEK ACE2 and VeroE6 cells with 2 mM PA. Four different variants of concern namely Alpha, Beta, Gamma or Delta were used to infect HEK ACE2 (0.1 MOI) and Vero E6 (0.001 MOI) cells as mentioned above. After 48 hr infection, total viral RNA copy number from infected cells was estimated by qRT PCR. VeroE6, Calu3 and HEK ACE2 cells were seeded in 24-well cell culture dishes to reach 80% confluency post 24 hr. Cells were then pre-treated with 2 mM PA in triplicates for 3 hr and infected with 100 µL per well 0.1 MOI SARS CoV-2 Hong Kong strain diluted in complete DMEM in the presence of drug. After 1 hr adsorption, media in wells were topped up with 400 µL DMEM containing 2 mM PA. Viral copy number from infected cells was estimated by qRT PCR 48 hr post infection.

Quantification of SARS-CoV-2 Viral Load by qRT PCR

Cells were harvested in TRIzol (15596018, Thermo Fisher) as per manufacturer's instruction. Equal amount of RNA was used to determine viral load using AgPath-ID™ One-Step RT-PCR kit (AM1005, Applied Biosystems). The following primers and probes targeting the SARS CoV-2 N-1 gene were used for amplification. Forward primer: 5'GACCCCAAAATCAGCGAAAT3' and Reverse primer: 5' TCTGGTTACTGCCAGTTGAATCTG3', Probe: (6-FAM/BHQ-1) ACCCCGCATTACGTTTGGTGGACC). The Ct values were used to determine viral copy number by generating a standard curve using SARS CoV-2 genomic RNA standard.

Multicycle IAV Infection

MDCK cells were seeded in 24-well cell culture dishes to reach 80-90% confluency after 24 hr. Cells were treated with 0.2, 0.5, 1, and 2 mM PA for 3 hr, washed once with warm PBS and infected with 0.01 MOI of PR8, HALo, Cal/09 and X79 viruses in OptiMEM reduced serum media (31985088, Gibco) containing 1 µg/mL L-tosylamide-2-phenyl ethyl chloromethyl ketone (TPCK trypsin) (T1426, Sigma). The drug (2 mM PA) was present throughout the duration of experiment. After 48 hr, supernatants from wells were collected, centrifuged at 2.5×g to remove cell debris, and used for plaque assay.

IAV Plaque Assay

MDCK cells were seeded in 12-well plates to reach complete confluency after 24 hr. 10-fold dilutions of supernatants collected from the multicycle experiment were prepared in OptiMEM and 100 µL per well was used to infect cells for 1 hr at 37° C. with regular shaking every 10 min. Virus inoculum was then removed and cells were overlaid with 1 mL MEM containing 0.6% oxoid agar (LP0028, Thermo Scientific) and 1 µg/mL TPCK trypsin. After 48 hr, cells were fixed with 4% formalin and plaques visualized by crystal violet staining.

Reporter Virus Infection Assay

A549 cells at 80-90% confluency in a 24-well dish were treated with 2 mM PA for 3 hr in triplicates. Cells were then washed and infected with 1 µL per well of Dengue Luc or Zika Luc; 0.2 µL per well HPIV Luc or 1 µL per well HSV Luc. 2 mM PA was present/not in the medium throughout the duration of experiment. After 48 hr, the cells harvested for detection of firefly and renilla luciferase expression using Dual-Luciferase Reporter Assay System (E1980, Promega) as per manufacturer's instructions. Luminescence measurements were taken using a TECAN Infinite 200-PRO multiplex reader.

Influenza Virus Infection Studies in Mice Model and Histopathology

Healthy 4-6 weeks old female BALB/c mice (Biogen Laboratory Animal Facility, Bengaluru, India) in groups of 4 were housed in individually ventilated cages (IVC) maintained at 23±1° C. temperature and 50±5% relative humidity. Animals were given access to standard pellet feed and water ad libitum and maintained on a 12-hour day/night light cycle at the Viral Biosafety level-3 facility, Indian Institute of Science. Animals were treated with 20 or 100 mg/kg PA by either intraperitoneal (IP) or oral routes. One group served as PBS (untreated) control. The body weight and general health of animals was measured every day for up to 9 days post treatment. Treatment groups were divided into two, one groups receiving 20 mg/kg PA prophylactically and the other, therapeutically. For infection, mice under intraperitoneal (IP) Ketamine (90 mg/kg) (Bharat Parenterals Limited) and Xylazine (4.5 mg/kg) (21, Indian Immunologicals Ltd) anesthesia were challenged intranasally with 50 PFU of PR8 WT virus in 40 µL PBS. Two dosage regimens and routes of drug administration were followed for the treatment of animals. Prophylactic treatment used administration of 20 mg/kg/day PA via oral or IP route during 6 hr before infection and therapeutic dosage (oral/IP) involved administering the same amount of drug 3 hr post infection. One half of the animals were sacrificed at 4 dpi and lungs collected for plaque assay quantification of IAV and histology analysis. For remaining animals, total bodyweight and survival was recorded until end of the experiment at 7 dpi. For plaque assay, lung samples were collected in DMEM containing 0.3% BSA, homogenized and centrifuged at 5000×g for 10 min at 4° C. to pellet tissue debris. The supernatant was used for plaque assay as mentioned previously. Lung samples were collected in 10% buffered formalin for histology analysis, processed and tissue sections of 4-6 µm thickness made using a microtome. The sections were then stained with Hematoxylin and Eosin and examined by light microscopy as previously described (Chan et al., 2020). Three different clinical criteria were observed, namely: vascular infiltration, alveolar infiltration, and interstitial pneumonia. Scoring was done based on severity on a scale of 1-4 (1-mild, 2-moderate, 3-severe, 4-very severe).

Pseudotyped SARS CoV-2 Particle Production and Transduction

Pseudotyped particles bearing the SARS-CoV-2 spike protein were produced as reported before (Crawford et al., 2020). Briefly, HEK 293T cells were seeded in 10 cm cell culture dishes to reach 50-60% confluency post 24 hr and transfected with 2.5 µg each of the following plasmids HDM-IDTSpike-fix (BEI, NR-52514); pHAGE-CMV-Luc2-IRES-ZsGreen-W (BEI, NR-52516); HDM-Hgpm2 (BEI, NR-52517); HDM-tat1b (BEI, NR-52518) and PRC-CMV-Rev1b (NR-52519) using Lipofectamine-2000 transfection agent (Invitrogen, 11668019). The supernatants were pooled together 60 hr post-transfection, centrifuged at 18×g for 10 min at 4° C. to remove cell debris, and finally passed through a 0.45 µm syringe filter before being used for transduction.

HEK ACE2 and Calu3 cells were seeded in 96-well dishes to reach 60-70% confluency after 24 hr. Cells were treated with 2, 1, 0.5, and 0.2 mM PA and 3 hr later, transduced with 100 µL per well pseudotyped SARS CoV-2 particles containing 5 µg/mL polybrene (Merck, TR-1003-G). The different concentrations of PA were present throughout the experiment. Post transduction (60 hr), cells were washed once with PBS and processed for detecting luciferase expression using a Firefly luciferase assay kit (Promega, E4550) as per the manufacturer's instructions. Luminescence measurements were taken using a TECAN Infinite 200-PRO multiplex reader.

Adeno Associated Virus-6 Production and Infection

AAV6 production: AAV6 particles were produced as per a previously published protocol (Negrini et al., 2020) with few modifications. Briefly, HEK 293T cells were seeded in 2×T75 flasks to reach 50-60% confluency the next day. For each flask, the following plasmids were transfected using Lipofectamine 2000 as per manufactures instructions: 17.7 µg pAdDeltaF6 (Addgene 112867), 7.9 µg pRepCap6 (Addgene 110770) and 5.9 µg pAAV-CAG-GFP (Addgene 37825). After 60 hr, the cells and medium mixture were pooled and transferred to a 50 mL conical tube. 3 mL Chloroform was added, vortexed gently for 5 min and 8 mL 5M NaCl was added. The tube was then centrifuged for 5 min at 3000×g, 4° C. and aqueous phase transferred to a fresh tube. 10 mL of 50% (v/v) PEG 8000 was added, vortexed briefly and incubated for 1 hr on ice before centrifuging for 30 min at 3000×g, 4° C. The supernatant was then discarded, pellet re-suspended in 1.5 mL HEPES, vortexed for 2 min and following components added: 3.5 µL of 1M MgCl2; 14 µL DNase I (NEB, M0303S) and 1.4 µL of 10 µg/µL RNase A (Thermo, EN0531). The contents were incubated for 20 min at 37° C., equal volume to chloroform added to the tube and mixed well before centrifuging for 5 min at 3000×g. Aqueous phase was then transferred to a new tube, followed by which the contents were passed through a 100 kDa Amicon Ultra Centrifugal Filter (Merck-Millipore, UFC510008) by centrifugation for 5 min at 14,000×g. The column was washed twice with PBS and AAV particles eluted into a fresh tube by centrifugation at 1000×g for 2 min.

Infection with AAV6 particles: HEK 293T cells were seeded in a poly-L-lysine coated 24-well dish to reach 60-70% confluency the next day. Cells were pre-treated or not with 2 mM PA for 3 hr and infected with 100 uL complete DMEM per well containing three different volumes i.e 2, 5 and 10 µl AAV6 particles. After 1 hr, medium was topped up with 400 µl complete DMEM. PA was present in the medium for entire duration of the experiment. After 48 hr, cells were trypsinized and re-suspended in PBS containing 3% FBS (FACS buffer). The number of GFP positive cells was analyzed using a Cytoflex (Beckman Coulter) flow cytometer and results analyzed using CytExpert software.

Adenovirus 5 Infection

For infection studies, HEK cells were pre-treated for 3 hr with 2 mM PA and infected with 10 MOI AAV5-eGFP in the presence of drug. After 24 hr, cells were trypsinized, re-suspended in FACS buffer and used to quantify total number of GFP positive cells by flow cytometry analysis. Drug was present in the treated conditions throughout the duration of experiment.

Flavivirus Infection

Confluent A549 cells in 24-well cell culture plate were pre-treated for 3 hr with 2 mM PA and infected with 100 µL per well DMEM containing 0.1 MOI JEV clinical strain P20778 or ZIKV Cambodia. After 1 hr adsorption, the wells were topped up with 400 µL DMEM. Drug (2 mM PA) was present in the media throughout the duration of experiment. Cells were then washed with PBS and harvested for western blot analysis 48 hr post infection. The separated proteins were transferred onto PVDF membrane and probed using mouse anti Flavivirus envelope 4G2 primary antibody and anti-mouse-HRP conjugated secondary antibody. Actin labelling using Mouse mAb to beta Actin-HRP (Abcam, ab49900) was used as loading control.

SARS-CoV-2 Spike Induced Syncytia Assay

Vero E6 cells were seeded in a 10 cm cell culture dish to reach 50-60% confluency after 24 hr. Cells were transfected with 5 µg plasmid expressing SARS-Related Coronavirus 2, Wuhan-Hu-1 Spike Glycoprotein (BEI resources NR-52514) using Lipofectamine 2000 transfection reagent (Invitrogen, 11668019), as per manufacturer's instructions. After 24 hr, cells were trypsinized and mixed with equal number of normal un-transfected Vero E6 cells to form a homogenous cell suspension. These cells were then seeded in a 24 well-cell culture dish containing glass coverslips, at a density of 1,00,000 cells per well. After 1 hr, cells were treated with 0.25, 0.5, 1 and 2 mM PA in triplicates, and incubated at 37° C., 5% CO2. Non-treated cells and normal un-transfected Vero E6 cells serves as positive and negative controls respectively. After 24 hr incubation, the cell culture plate was placed on ice to arrest endocytosis. Cells were then washed once with cold PBS and incubated with 10 µg/mL Wheat Germ Hemagglutinin (WGA) (Invitrogen, W11261) for 3 min, after which cells were fixed with 4% PFA for 10 min. This was followed by incubation of cells in PBS containing 0.1 µg/mL DAPI (Sigma Aldrich, D9542) for 10 min to label nuclei. Finally, cells were washed with PBS and the coverslips were mounted on glass slides using ProLong Diamond Antifade Mountant (Invitrogen, P36970). Cells were imaged using an EVOS M5000 fluorescence microscope and the area of syncytia across different conditions were quantified by drawing ROIs using Imagej/Fiji.

Coxsackie and Rotavirus Infections

Coxsackie virus B3 infection: To study early effects of PA, HeLa cells were pre-treated for 3 hr, infected with 10 MOI CVB3, and collected at 3 hr post infection. Alternatively, cells were infected and treated simultaneously (T0) and collected after 3 hr. Also, a mixture of virus and drug incubated for 1 hr (1 hr PA+Virus) was used for infection to test the effects of PA on virus particles. No additional drug was added here post infection. Expression levels of VP1 protein was then detected by western blot analysis.

Rotavirus RRV infection: A working concentration of Rota virus was prepared by diluting the virus stock 2-fold with complete DMEM containing a final concentration of 2 µg/mL TPCK trypsin. The mixture was incubated at 37° C. for 30 min and further diluted 2-fold in DMEM without serum. This mixture was then used to infect HEK cells that were pre-treated for 3 hr with 2 mM PA. A volume of 100 µL per well, in a 24 well plate was used for 1 hr adsorption, after which the wells were topped up with 400 µL serum free media containing PA. After 12 hr, cells were fixed with 4% formalin and immunolabeled with primary mouse anti VP6, and anti-mouse secondary Alexa Fluor 488 antibodies to detect virus infected cells by IFA.

Influenza Virus Membrane Fusion Assay

Virus labelling: IAV particles were labelled using Octadecyl Rhodamine B Chloride (R18) as reported earlier, with minor modifications (Hoekstra et al., 1984). A total volume of 1 mL PR8 wild type virus ($2 \times 10^9$ PFU/mL, titrated by plaque assay) was centrifuged at 2.5×g for 5 min to remove any debris, and placed on ice. R18 dye was added to the virus at 20 µM final concentration while simultaneously subjecting to continuous vortexing for 2 min, followed by which the virus-dye mixture was incubated for 60 min on a rocker at RT. After a further 60 min incubation ice, the preparation was centrifuged at 25,000×g for 3 hr at 4° C. to remove unbound dye. Finally, the concentrated R18 labelled virus preparation was carefully removed from the tube and re-suspended in 200 µL NTC buffer (100 mM NaCl, 20 mM Tris-HCl pH 7.4, 5 mM $CaCl_2$).

Membrane fusion assay: The methodology for detection of IAV membrane fusion in endosomes was adapted from a previously reported protocol, with few modifications (Hoffmann et al., 2018), Briefly, MDCK cells in suspension were pre-treated/not for 3 hr with 2 mM PA, 10 µM ammonium chloride ($NH_4Cl$) or 10 µM Chloroquine (CQ) at 37° C. Cells were then washed with ice cold PBS and infected with 10 MOI R18 labelled virus in OptiMEM containing 1 µg/mL TPCK trypsin, and placed on ice. Post 1 hr adsorption, cells were transferred to a pre-chilled opaque flat bottom 96-well cell culture plate (136101, Nunc) and placed in a TECAN Infinite 200-PRO multiplex reader pre-set at 37° C. Fluorescence intensity measurements (Ex 560/Em 590) were recorded at every 5 min interval for up to 90 min.

Characterizing Effects of PA on Endocytosis

Transferrin uptake assay: A549 cells in a 24 well dish were treated or not with 2 mM PA for 2 hr followed by washing of cells with PBS and starvation for 1 hr in the presence of DMEM without FBS for 1 hr. Cells were then washed and incubated with 25 µg/mL Transferrin Alexa Fluor 647 Conjugate (T23366, Invitrogen) for 1 hr. PA was present during the entire course of experiment. Finally, cells were washed twice with PBS, trypsinized and re-suspended in PBS containing 0.03% BSA for analysis in a Cytoflex flow cytometer. Results were analyzed using CytExpert software.

Localization of transferrin labelled vesicles: Vero cells were seeded on glass coverslips in a 12 well dish to reach 70-80% confluency next day. After 3 hr treatment/not with 2 mM PA, cells were washed once with ice cold PBS and the plate was placed on ice for 10 min before incubating with OptiMEM containing PR8 wild type virus (100 MOI) and 25 µg/mL Transferrin 647 (Tf-647) for 1 hr on ice. Cells were washed twice with PBS and the plate moved to 37° C. After a 15 min chase, cells were fixed with 4% PFA, labelled with anti influenza virus HA antibody (PY102) followed by anti-mouse Alexa 488 secondary antibody to label the virus particles. Nuclei were labelled using 0.1 µg/mL DAPI. Images were acquired using a Zeiss LSM-880 Multiphoton microscope.

The dispersion of transferrin labelled vesicles from perinuclear region to cell periphery was quantified by drawing region of interests (ROIs) up to 20 µm away from the nuclei. The fluorescence intensity of Tf-647 labelled vesicles was then measured along this distance using ImageJ/Fiji.

Drug Cytotoxicity Assay

A549 cells were seeded in 96-well cell culture dishes and 24 hr later treated with 0.02, 0.2, 2, and 20 mM PA in triplicates. Cells were then incubated at 37° C., 5% CO2, and cytotoxicity was measured at 12, 24, 36, 48, 60, and 72 hr post-treatment using AlamarBlue™ Cell Viability Reagent (DAL 1025, Thermo Fisher) as per manufacturer's instructions.

Similarly, cytotoxicity assay in MDCK cells measured at 48 hr post-treatment was done using 0.2, 0.5, 1, and 2 mM PA, in parallel with the multicycle IAV infection experiment mentioned below.

IAV Time of Addition Assay

A549 cells were seeded in 24-well cell culture plates containing (or not) glass coverslips to reach 70-80% confluency the next day. For infection, cells were washed once with warm PBS and incubated with 100 µL per well PR8 WT virus (2 MOI) diluted in OptiMEM. The plates were tilted at every 10 min to ensure even distribution of inoculum. After 1 hr adsorption, the medium in wells were topped up with 400 µL OptiMEM. Effects of PA on early and late events during IAV infection was studied at 3 and 9 hr time points p.i, respectively. In the former, cells were pre-treated with 2 mM PA for 3 hr, infected and collected at 3 hr post infection. Alternatively, PA treatment was done only at 6 hr post infection and cells were harvested after a further 3 hr incubation period. Direct effect of the drug on virus particles was studied by incubating virus inoculum in OptiMEM containing 2 mM PA at 37° C. for 60 min, followed by which the virus-drug mixture was used to infect cells as mentioned above. Post 1 hr adsorption, the medium was topped up with 400 µL OptiMEM without drug. In all cases, cells were harvested for both IFA and western blot analysis.

Immunofluorescence assay: Cells on glass coverslips were washed once with PBS, fixed with 4% PFA for 10 min and permeabilized for 10 min with PBS containing 1% Tween-20. Cells were then washed and incubated in blocking buffer (PBS with 0.3% Tween 20, 2% BSA) for 1 hr. Overnight incubation with primary antibody Anti-mouse Influenza virus NP (HT103) diluted in blocking buffer was followed by washing and incubation with Goat anti-Mouse IgG (H+L) Cross-Adsorbed Secondary Antibody, Alexa Fluor 488 (A11001, Invitrogen) in blocking buffer containing 0.1 µg/mL DAPI (D9542, Sigma). Finally, cells were incubated with PBS containing 50 mM ammonium chloride for de-quenching, washed, and the cells on coverslips were mounted on glass slides using ProLong™ Diamond Antifade Mountant (Molecular Probes, P36961). Images were acquired using an EVOS M5000 Imaging system. Quantification of NP positive cells relative to the total number of DAPI positive cells in 5 different fields was performed using ImageJ/Fiji software.

Western Blot: Cells were washed with 1×PBS (162528, MP Biomedicals), lysed with 1× Laemmli buffer (1610747, BIO-RAD), and heated at 95° C. for 10 min. Cell lysates were then subjected to standard SDS-PAGE and separated proteins were transferred onto a PVDF membrane (IPVH00010, Immobilon-P; Merck). The membrane was incubated in blocking buffer containing 5% Skimmed milk (Sigma-Aldrich, 70166) in 1×PBS containing 0.05% Tween 20 (P1379, Sigma-Aldrich) (1×PBST) for 2 hr with slow rocking at room temperature (RT). Primary antibody Anti-mouse Influenza virus NP (HT103) incubation in blocking buffer was done for 14 hr at 4° C. with gentle rocking, after which the membrane was washed with 1×PBST and incubated for 2 hr with secondary antibody Goat Anti-Mouse IgG-H&L Polyclonal Antibody, HRP conjugated (Abcam, ab6789) in blocking buffer at RT. After a further wash with 1×PBST, the blots were developed using Clarity Western ECL Substrate (Bio-Rad, 1705061).

SARS CoV-2 Time of Addition Assay

VeroE6 and HEK ACE2 cells were seeded in 24-well cell culture plates containing glass coverslips to reach 70-80% confluency the next day. For infection, cells were washed once with warm PBS and incubated with 100 µL per well 10 MOI SARS CoV-2 diluted in complete DMEM. The plates were tilted at every 10 min to ensure even distribution of inoculum. After 1 hr adsorption, the media in wells were topped up with 400 µL OptiMEM. Effects of PA on early and late events during SARS CoV-2 infection was studied at 3 and 9 hr time points p.i, respectively. In the former, cells were pre-treated with 2 mM PA for 3 hr, infected and collected at 3 hr post infection. Alternatively, cells were infected and treated simultaneously (T0) and collected after 3 hr. The drugs effect on late events was studied by treating cells only during 6 hr post infection, after which cells were harvested after 3 hr. Once added, PA was present in the medium throughout the remaining duration of experiment. In all cases, cells were harvested for both IFA and western blot analysis.

The antibodies used for IFA included SARS-CoV-2 spike primary antibody (GTX632604, GeneTex) and goat anti-Mouse IgG (H+L) Cross-Adsorbed Secondary Antibody, Alexa Fluor 488 (Invitrogen, A-11001). Quantification of spike positive cells was done using ImageJ/Fiji.

Western blot analysis of viral proteins used Polyclonal Anti-SARS-Related Coronavirus 2 Spike Glycoprotein (BEI, NR-52947) and Goat Anti-Rabbit IgG-H&L Polyclonal antibody, HRP Conjugated (Abcam, ab6721).

Transmission Electron Microscopy

PR8 WT virus of stock titer 2×109 PFU/mL made in chicken eggs was passed through 0.45 µm syringe filter and concentrated by ultracentrifugation at 25,000×g for 2 hr at 4° C. The concentrated virus prep was then divided into three parts incubated with (a) 2 mM Picolinic acid (b) Positive control—0.01% TritinX100 and (c) Negative control—distilled water. Aliquots (2-3 µL) of the virus samples were applied to a Formvar/carbon covered copper grid (Ted Pella, 01813,) which was hydrophilized by glow discharging at 8 W for 60 s directly before use. After 2 min, excess sample was removed using Whatman filter paper. 5 µL of negative stain 2% uranyl acetate (Ted Pella, 19481) was added on to the grid and incubated for 40 secs, after which excess stain was removed. Negative staining step was repeated for 3 times and grid was air-dried for 10 min before imaging. The grids were imaged using a Talos L120C transmission electron microscope equipped with a LaB6 electrode operating at an acceleration voltage of 120 kV. Images of the virus were recorded using a 4 k Å~4 k Ceta CMOS camera.

Mycobacteria and TM4 Bacteriophage Experiments

Bacterial culture and passage: Primary *Mycobacterium smegmatis* (mc2 155) (a kind gift from Prof. Deepak Saini, Indian Institute of Science) was grown in Middlebrook 7H9 broth (Merck, M0178) supplemented with Glycerol (Fisher scientific, Q24505), ADC (HiMedia, FD019), and 0.1% v/v Tween 80 (Fisher Scientific, YBP338500). A log phase primary culture was inoculated into a secondary culture without Tween-80 and supplemented with 2 mM CaCl2 (Fisher scientific, Q12135) to promote efficient infection of phages.

Bacteriophage: TM4 mycobacteriophage was amplified in *M. smegmatis* and phage enumeration was done using the soft agar overlay technique as reported by Kalapala et al (Kalapala et al., 2020).

Bacterial toxicity assay: PA stock solution of 1M concentration was prepared in sterile deionized water and diluted to obtain different concentrations (1 mM, 5 mM, 10 Mm, 20 mM, and 40 mM), in a 48-well plate. A total of $2 \times 10^5$ cells of *M. smegmatis* were added to each of the wells. The 48-well plate was placed in a rotary shaker incubator at 37° C. for 24 h. Readings were taken periodically using a Tecan Spark multi-mode plate reader at 600 nm.

Effect of drug on TM4 mycobacteriophage: To study the effect of the drug on TM4 phage growth and activity, 7H9 broth supplemented with ADC and CaCl2 was prepared and inoculated with 100 µL of log-phase secondary bacterial culture (OD 1-2) per 5 mL of the media. 1 mM of the drug was added to culture tubes at the appropriate time (either at the start of the experiment or 3 hr before adding the phage in the mid-log phase). The cultures were then incubated at 37° C. with rotary shaking at 180 pm. For phage-treated samples, a 10 MOI TM4 mycobacteriophage was added at a specified interval of the mid-log phase. For optical density (OD) measurements, 100 µL of bacterial culture at various time intervals was diluted 10 times in media and pipetted several times to obtain a uniform cell suspension. Readings were taken using a spectrophotometer (Jenway 7205 UV/Visible Spectrophotometer) at 600 nm against a media blank.

SARS CoV-2 Infection Studies in the Hamster Model

All animal experiments involving SARS CoV-2 infection were performed in 10-12-week-old mixed-gender Syrian golden hamsters (Biogen Laboratory Animal Facility Bengaluru, India). Males and female hamsters were housed separately in individually ventilated cages (IVC) maintained at 23±1° C. temperature and 50±5% relative humidity, given access to standard pellet feed and water ad libitum, and maintained on a 12-hour day/night light cycle at the Viral Biosafety level-3 facility, Indian Institute of Science. An overdose of Ketamine (Bharat Parenterals Limited) and Xylazine (Indian Immunologicals Ltd) was used to sacrifice animals upon completion of the experiment. Experimentally, hamsters under intraperitoneal (IP) Ketamine (150 mg/kg) (Bharat Parenterals Limited) and Xylazine (10 mg/kg) (21, Indian Immunologicals Ltd) anesthesia were challenged intranasally with 105 plaque forming units (PFU) SARS CoV-2 in 100 µL PBS. Two dosage regimens and routes of drug administration were followed for the treatment of animals. The prophylactic treatment used administration of 20 mg/kg/day PA via oral or IP route during −3, −2, and −1 day before infection and therapeutic dosage (oral/IP) involved administering 20 mg/kg/day PA during 1, 2 and 3-day post-infection (dpi). A total volume of 200 µL PA dissolved in PBS was used for both oral and IP routes of administration. Total lungs were harvested, weighed, and processed for histopathological analysis. One portion was used for RNA extraction using Trizol and subsequent viral RNA copy number estimation by qRT PCT as described previously.

Histopathology of Hamster Lung Tissue:

Lung tissue samples were fixed in 4% paraformaldehyde (PFA), embedded in paraffin blocks and tissue sections of 4-6 μm thickness made using a microtome. The sections were then stained with Hematoxylin and Eosin and examined by light microscopy as previously described (Chan et al., 2020). Clinical scoring was done based on three different criteria namely: Alveolar edema; vascular and perivascular infiltration; alveolar thickening and infiltration. Scoring was done based on severity on a scale of 1-4 (1-mild, 2-moderate, 3-severe, 4-very severe).

NUMBERED EMBODIMENTS

1. A method for inhibiting entry of a virus into a host cell, comprising contacting the host cell with picolinic acid or a salt or derivative thereof.
2. The method of Embodiment 1, wherein the virus is an enveloped virus.
3. The method of Embodiment 2, wherein the enveloped virus is SARS-CoV-2, parainfluenza, influenza, Japanese encephalitis virus, Zika virus, or a flavivirus.
4. The method of Embodiment 1, wherein the virus a syncytium-forming virus.
5. The method of Embodiment 4, wherein the syncytium-forming virus is selected from Coronaviridae (e.g., SARS-CoV-2, MERS, SARS-CoV etc.), Herpesviridae (HSV, HCMV etc.), Paramyxoviridae (Nipah, Hendra, Measles, RSV etc.), Retroviridae (HIV, HTLV etc.), Hepatitis C Virus, Ebola, Sendai, Reovirus (e.g., Orthoreoviruses and Aquareoviruses).
6. The method of any one of Embodiments 1-5, wherein the salt is selected from zinc picolinate, chromium picolinate, iron picolinate, sodium picolinate, or a combination thereof.
7. The method of any one of Embodiments 1-5, wherein the derivative is fusaric acid or a compound comprising substitutions at the 3, 4, 5 and/or 6 positions of picolinic acid.
8. The method of any one of Embodiments 1-7, wherein the host cell is a mammalian cell, an avian cell, or a plant cell.
9. A method for treating or preventing a viral infection in a subject, comprising administering to the subject picolinic acid or a salt or derivative thereof.
10. The method of Embodiment 9, wherein the viral infection is caused by an enveloped virus.
11. The method of Embodiment 10, wherein the enveloped virus is SARS-CoV-2, parainfluenza, influenza, Japanese encephalitis virus, Zika virus or a flavivirus.
12. The method of Embodiment 9, wherein the viral infection is caused by a syncytium-forming virus.
13. The method of Embodiment 12, wherein the syncytium-forming virus is selected from Coronaviridae (e.g., SARS-CoV-2, MERS, SARS-CoV etc.), Herpesviridae (HSV, HCMV etc.), Paramyxoviridae (Nipah, Hendra, Measles, RSV etc.), Retroviridae (HIV, HTLV etc.), Hepatitis C Virus, Ebola, Sendai, Reovirus (e.g., Orthoreoviruses and Aquareoviruses).
14. The method of any one of Embodiments 9-13, wherein the salt is selected from zinc picolinate, chromium picolinate, iron picolinate, sodium picolinate, or a combination thereof.
15. The method of any one of Embodiments 9-13, wherein the derivative is fusaric acid or a compound comprising substitutions at the 3, 4, 5 and/or 6 positions of picolinic acid.
16. The method of any one of Embodiments 9-15, wherein the picolinic acid or the salt or derivative thereof is administered via a route of administration selected from the group consisting of oral, parenteral, intranasal, inhalation, nebulization, and topical.
17. The method of Embodiment 16, wherein the route of administration is oral.
18. The method of Embodiment 16, wherein the route of administration is intranasal.
19. The method of any one of Embodiments 9-18, wherein about 3 mg to about 100 mg of picolinic acid or the salt or derivative thereof is administered to the subject per kilogram of body weight per day.
20. The method of any one of Embodiments 9-19, wherein the subject is a mammal, bird, or plant.
21. Picolinic acid or a salt or derivative thereof for use in inhibiting entry of a virus into a host cell.
22. Picolinic acid or a salt or derivative thereof for use as recited in Embodiment 21, wherein the virus is an enveloped virus.
23. Picolinic acid or a salt or derivative thereof for use as recited in Embodiment 22, wherein the enveloped virus is SARS-CoV-2, parainfluenza, influenza, Japanese encephalitis virus, Zika virus, or a flavivirus.
24. Picolinic acid or a salt or derivative thereof for use as recited in Embodiment 21, wherein the virus is a syncytium-forming virus.
25. Picolinic acid or a salt or derivative thereof for use as recited in Embodiment 21, wherein the syncytium-forming virus is selected from Coronaviridae (e.g., SARS-CoV-2, MERS, SARS-CoV etc.), Herpesviridae (HSV, HCMV etc.), Paramyxoviridae (Nipah, Hendra, Measles, RSV etc.), Retroviridae (HIV, HTLV etc.), Hepatitis C Virus, Ebola, Sendai, Reovirus (e.g., Orthoreoviruses and Aquareoviruses).
26. Picolinic acid or a salt or derivative thereof for use as recited in any one of Embodiments 21-25, wherein the host cell is a mammalian cell, an avian cell, or a plant cell.
27. Picolinic acid or a salt or derivative thereof for use as a medicament for treating or preventing a viral infection in a subject.
28. Picolinic acid or a salt or derivative thereof for use as recited in Embodiment 27, wherein the viral infection is caused by an enveloped virus.
29. Picolinic acid or a salt or derivative thereof for use as recited in Embodiment 28, wherein the viral infection is a SARS-CoV-2, parainfluenza, influenza, Japanese encephalitis virus, Zika virus, or a flavivirus infection.
30. Picolinic acid or a salt or derivative thereof for use as recited in Embodiment 27, wherein the viral infection is caused by a syncytium-forming virus.
31. Picolinic acid or a salt or derivative thereof for use as recited in Embodiment 30, wherein the syncytium-forming virus is selected from Coronaviridae (e.g., SARS-CoV-2, MERS, SARS-CoV etc.), Herpesviridae (HSV, HCMV etc.), Paramyxoviridae (Nipah, Hendra, Measles, RSV etc.), Retroviridae (HIV, HTLV etc.), Hepatitis C Virus, Ebola, Sendai, Reovirus (e.g., Orthoreoviruses and Aquareoviruses).

32. Picolinic acid or the salt or derivative thereof for use as recited in any one of Embodiments 21-31, wherein the salt is selected from zinc picolinate, chromium picolinate, iron picolinate, sodium picolinate, or a combination thereof.

33. Picolinic acid or the salt or derivative thereof for use as recited in any one of Embodiments 21-31, wherein the derivative is fusaric acid or a compound comprising substitutions at the 3, 4, 5 and 6 positions of picolinic acid.

34. Picolinic acid or the salt or derivative thereof for use as recited in any one of Embodiments 27-33, wherein the medicament is administered via a route of administration selected from the group consisting of: oral, parenteral, intranasal, inhalation, nebulization, and topical.

35. Picolinic acid or the salt or derivative thereof for use as recited in any one of Embodiments 27-33, wherein the medicament is administered orally or intranasally.

36. Picolinic acid or the salt or derivative thereof for use as recited in any one of Embodiments 27-35, wherein the medicament comprises 1 to 500 mg of picolinic acid or the salt or derivative thereof in a unit dose.

37. Picolinic acid or the salt or derivative thereof for use as recited in any one of Embodiments 27-36, wherein the subject is a mammal, bird, or plant.

38. An oral pharmaceutical composition comprising picolinic acid or a salt or derivative thereof and a pharmaceutically acceptable excipient.

39. A parenteral pharmaceutical composition comprising picolinic acid or a salt or derivative thereof and a pharmaceutically acceptable excipient.

40. An intranasal pharmaceutical composition comprising picolinic acid or a salt or derivative thereof and a pharmaceutically acceptable excipient.

41. A dietary supplement comprising picolinic acid or a salt or derivative thereof.

42. A horticultural or agricultural composition comprising picolinic acid or a salt or derivative thereof and a horticulturally or agriculturally acceptable excipient.

43. A method for treating a viral infection in plants comprising, contacting a plant cell with picolinic acid or a salt or derivative thereof.

44. The method of Embodiment 43, wherein the viral infection is caused by a virus from a virus family selected from the group consisting of Geminiviridae (e.g., Cassava Mosaic Virus, Maize streak virus); Caulimoviridae (e.g., Banana streak virus, Rice Tungro Bacilliform virus); Potyviridae (e.g., Sugarcane mosaic virus, Maize dwarf mosaic virus, Sweet potato feathery mottle virus); Tombusviridae (e.g., Barley yellow dwarf viruses); Bromoviridae (e.g., Cucumber mosaic virus); and Nanoviridae (e.g., Banana bunchy top virus).

The invention claimed is:

1. A method for inhibiting entry of a virus into an uninfected host cell in a host, comprising treating the host with picolinic acid or a salt or derivative thereof, wherein said treating inhibits entry of the virus into the uninfected host cell by blocking viral and cellular membrane fusion.

2. The method of claim 1, wherein the virus is an enveloped virus.

3. The method of claim 1, wherein the virus a syncytium-forming virus.

4. The method of claim 2, wherein the enveloped virus is SARS-COV-2, parainfluenza, influenza, Japanese encephalitis virus, Zika virus, or a flavivirus.

5. The method of claim 3, wherein the syncytium-forming virus is selected from Coronaviridae, Paramyxoviridae, Hepatitis C Virus, Ebola, Sendai, or Reovirus.

6. The method of claim 1, wherein the salt is selected from zinc picolinate, chromium picolinate, iron picolinate, sodium picolinate, or a combination thereof.

7. The method of claim 1, wherein the derivative is fusaric acid or a compound comprising substitutions at the 3, 4, 5 and/or 6 positions of picolinic acid.

8. The method of claim 1, wherein the host cell is a mammalian cell, an avian cell, or a plant cell.

9. The method of claim 1, wherein the host is treated with picolinic acid.

10. The method of claim 1, wherein the host is treated with a salt of picolinic acid.

11. The method of claim 1, wherein the virus is SARS-COV-2.

12. The method of claim 1, wherein the virus is parainfluenza virus.

13. The method of claim 1, wherein the virus is influenza virus.

14. The method of claim 1, wherein the virus is Japanese encephalitis virus.

15. The method of claim 1, wherein the virus is Zika virus.

16. The method of claim 1, wherein the virus is flavivirus.

* * * * *